United States Patent
Chavez et al.

(10) Patent No.: US 10,174,064 B2
(45) Date of Patent: Jan. 8, 2019

(54) PHOTOACTIVE ENERGETIC MATERIALS

(71) Applicant: Los Alamos National Security, LLC, Los Alamos, NM (US)

(72) Inventors: David E. Chavez, Ranchos de Taos, NM (US); Susan Kloek Hanson, Los Alamos, NM (US); Robert Jason Scharff, Los Alamos, NM (US); Jacqueline Marie Veauthier, Los Alamos, NM (US); Thomas Winfield Myers, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 15/868,562

(22) Filed: Jan. 11, 2018

(65) Prior Publication Data
US 2018/0237464 A1    Aug. 23, 2018

Related U.S. Application Data

(62) Division of application No. 14/713,807, filed on May 15, 2015, now Pat. No. 9,902,748.

(60) Provisional application No. 61/993,707, filed on May 15, 2014.

(51) Int. Cl.
| | |
|---|---|
| *C07D 257/08* | (2006.01) |
| *C07D 251/30* | (2006.01) |
| *C07D 251/34* | (2006.01) |
| *C06B 25/34* | (2006.01) |
| *C07F 15/02* | (2006.01) |
| *C07F 15/06* | (2006.01) |
| *C07F 15/04* | (2006.01) |
| *C07F 1/08* | (2006.01) |
| *C06B 41/00* | (2006.01) |
| *C07C 7/00* | (2006.01) |
| *C07C 9/00* | (2006.01) |
| *C06C 9/00* | (2006.01) |
| *C06C 7/00* | (2006.01) |

(52) U.S. Cl.
CPC ............ *C07F 15/065* (2013.01); *C06B 25/34* (2013.01); *C06B 41/00* (2013.01); *C07D 251/30* (2013.01); *C07D 257/08* (2013.01); *C07F 1/08* (2013.01); *C07F 15/025* (2013.01); *C07F 15/045* (2013.01); *C06C 7/00* (2013.01); *C06C 9/00* (2013.01)

(58) Field of Classification Search
CPC .... C06B 25/34; C07D 257/08; C07D 251/30; C07D 251/34
USPC ............... 544/179, 196, 197, 198, 204, 219; 149/91
See application file for complete search history.

(56) References Cited

U.S. PATENT DOCUMENTS

| | | |
|---|---|---|
| 3,244,702 A | 4/1966 | Marcus |
| 5,281,706 A | 1/1994 | Coburn et al. |

FOREIGN PATENT DOCUMENTS

GB          1195558 A  *  6/1970  ............. C06B 25/00

OTHER PUBLICATIONS

Matuszko et al. Journal of Organic Chemistry (1962), 27, 677-8.*
Hiskey et al. Journal of Energetic Materials (1999), 17(2 & 3), 233-252.*

* cited by examiner

*Primary Examiner* — Venkataraman Balasubramanian
(74) *Attorney, Agent, or Firm* — Klarquist Sparkman, LLP

(57) ABSTRACT

Energetic materials that are photoactive or believed to be photoactive may include a conventional explosive (e.g. PETN, nitroglycerine) derivatized with an energetic UV-absorbing and/or VIS-absorbing chromophore such as 1,2,4,5-tetrazine or 1,3,5-triazine. Absorption of laser light having a suitably chosen wavelength may result in photodissociation, decomposition, and explosive release of energy. These materials may be used as ligands to form complexes. Coordination compounds include such complexes with counterions. Some having the formula $M(L)_n^{2+}$ were synthesized, wherein M is a transition metal and L is a ligand and n is 2 or 3. These may be photoactive upon exposure to a laser light beam having an appropriate wavelength of UV light, near-IR and/or visible light. Photoactive materials also include coordination compounds bearing non-energetic ligands; in this case, the counterion may be an oxidant such as perchlorate.

6 Claims, 9 Drawing Sheets

PHOTOACTIVE ENERGETIC MATERIALS

BENEFIT CLAIM TO A RELATED APPLICATION

This application is a divisional of U.S. patent application Ser. No. 14/713,807, filed May 15, 2015, which in turn claims the benefit of U.S. Provisional Patent Application No. 61/993,707 entitled "Photoactive Energetic Materials," filed May 15, 2014, both of which are hereby incorporated by reference.

STATEMENT REGARDING FEDERAL RIGHTS

This invention was made with government support under Contract No. DE-AC52-06NA25396 awarded by the U.S. Department of Energy. The government has certain rights in the invention.

FIELD

The field relates to energetic materials and more particularly to energetic materials that are photoactive, or are believed to be photoactive, and will optically initiate (i.e. ignite) upon exposure to a suitable intense laser beam having a desired wavelength in the visible ("VIS"), near-infrared ("near-IR") or ultraviolet ("UV") region of the electromagnetic spectrum.

BACKGROUND

There is a demand for high explosives ("HE"), propellants, and other energetic materials that can be initiated more safely than by traditional thermal or electrical means. Using such energetic materials may, for example, prevent accidental electrostatic initiation. High explosives that can be optically initiated using ultraviolet or visible laser light may provide a solution. For at least some applications, these photoactive energetic materials could replace other more conventional explosives that tend to be more sensitive to mechanical and thermal stimuli. Explosive detonators, for example, could be configured for optical initiation using laser light of a suitably low energy (e.g. ultraviolet ("UV"), near-infrared ("near-IR"), or perhaps visible ("VIS") laser light).

Most high explosives cannot be optically initiated (i.e. are not photoactive) in the wavelength range for visible light. Conventional explosives such as RDX, HMX, and PETN do not absorb in the VIS and near-infrared regions, and absorb only weakly in the UV region. Their initiation using a laser is possible but typically requires much higher frequency laser light than VIS or UV laser light.

Energetic materials that may be optically initiated using relatively low energy laser light are desirable.

SUMMARY

An embodiment relates to a composition of the formula

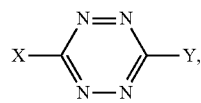

or of the formula

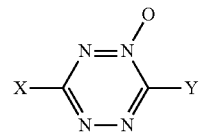

or of the formula

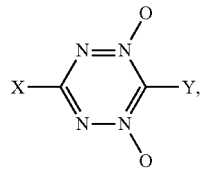

or of the formula

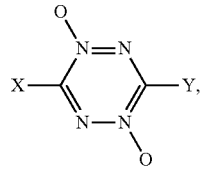

wherein X is chloride, bromide, or iodide, and
wherein Y is —OCH$_2$C(CH$_2$ONO$_2$)$_3$, —OCH$_2$C((F)(NO$_2$)$_2$), —OCH(ONO$_2$)$_2$,

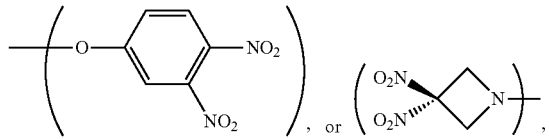

or
wherein X is

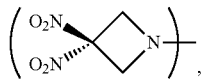

and
wherein Y is

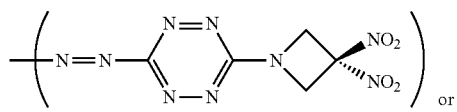

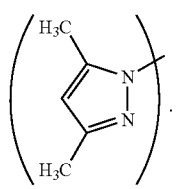

or wherein X and Y are each independently selected from —OCH$_2$C(CH$_2$ONO$_2$)$_3$, —OCH$_2$C((F)(NO$_2$)$_2$), —OCH(ONO$_2$)$_2$,

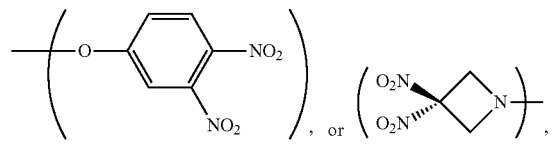

or NH$_2$, with the exception that if X is NH$_2$, then Y is not NH$_2$.

Another embodiment relates to a composition of the formula

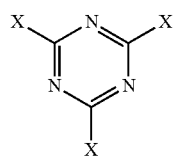

wherein X is selected from —OCH$_2$C(CH$_2$ONO$_2$)$_3$, —OCH$_2$C((F)(NO$_2$)$_2$), —OCH(ONO$_2$)$_2$,

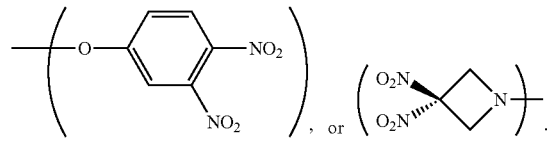

Another embodiment relates to a composition of the formula

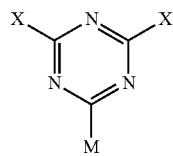

wherein X is selected from —OCH$_2$C(CH$_2$ONO$_2$)$_3$, —OCH$_2$C((F)(NO$_2$)$_2$), —OCH(ONO$_2$)$_2$,

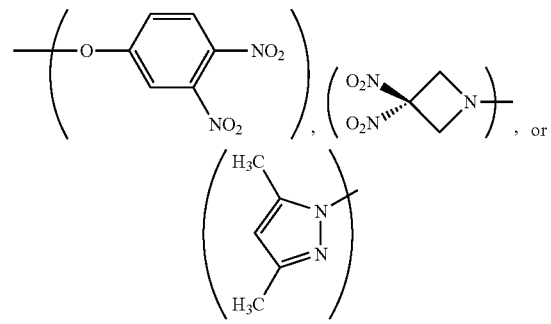

and wherein M is

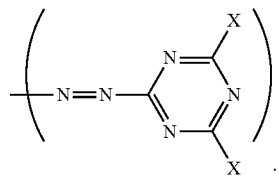

An embodiment also includes a composition of the formula

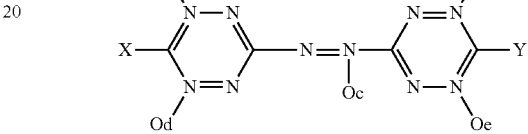

wherein the sum a+b+c+d+e equals 0, 1, 2, 3, 4, or 5, and wherein X and Y are each independently selected from —OCH$_2$C(CH$_2$ONO$_2$)$_3$, —OCH$_2$C((F)(NO$_2$)$_2$), —OCH(ONO$_2$)$_2$,

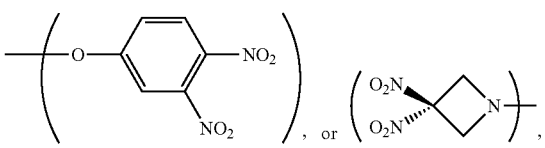

or NH$_2$.

An embodiment also includes a coordination compound comprising a cationic complex comprising a transition metal center; at least one ligand comprising a 1,2,4,5-tetrazine ring or a 1,3,5-triazine ring coordinated to the transition metal center; at least one explosive pendant group covalently bonded to the 1,2,4,5-tetrazine ring or 1,3,5-triazine ring; and a counterion.

An embodiment also includes a coordination compound comprising a cationic complex comprising a transition metal center; at least one ligand comprising a 1,2,4,5-tetrazine ring or a 1,3,5-triazine ring coordinated to the transition metal center; and perchlorate counterion.

An embodiment also includes a compound of the formula

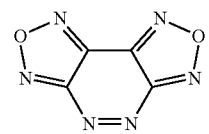 [SMILES: n1nc2nonc2c2nonc12]

or of the formula

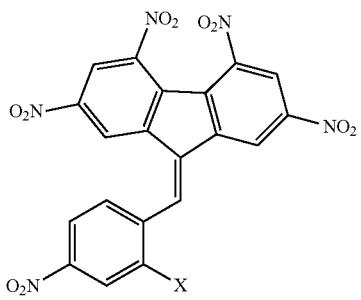

or of the formula

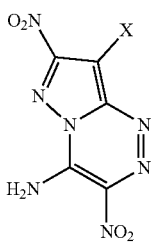

or of the formula

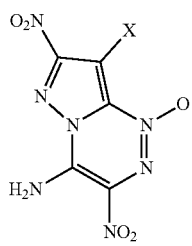

wherein X is H or NO$_2$.

BRIEF DESCRIPTION OF THE DRAWINGS

FIG. 3b also includes the spectra of FIG. 3a rotated clockwise 90 degrees.

DETAILED DESCRIPTION OF THE EMBODIMENTS

Figure 1:
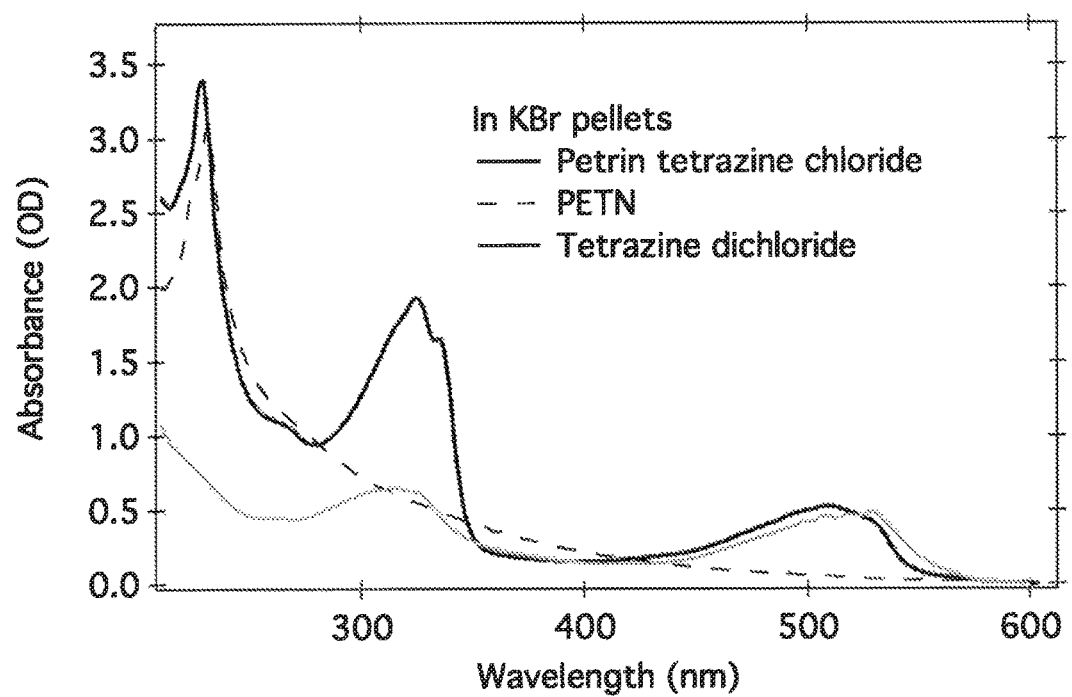
FIG. 1 shows UV-VIS spectra for PETN, compound 1 (1,2,4,5-tetrazine dichloride), and embodiment compound 2 (Petrin 1,2,4,5-tetrazine chloride).

Embodiment compositions are energetic materials that are photoactive, or are expected to be photoactive, and undergo photoinitiation when exposed to wavelengths of light in the ultraviolet ("UV"), near-infrared ("near-IR"), and/or visible region ("VIS") of the electromagnetic spectrum that are suitable for photoactivation. Some of the embodiment energetic materials were described by Chavez et al. in "Electroactive Explosives: Nitrate Ester-Functionalized 1,2,4,5-Tetrazines," Angew. Chem. Int. Ed., 2013, vol. 52, pp. 6876-6879, which was published on the web on May 16, 2013, and is incorporated by reference.

Some embodiments contain a chromophore such as a 1,2,4,5-tetrazine ("Tz") ring and/or a 1,3,5-triazine ring. These chromophores absorb energy in the ultraviolet and/or visible region. Tz rings typically have large heats of formation and high electron affinities. Tz rings are also electron-poor, with a typically forbidden n-π* transition for the Tz ring. Tetrazines range in color from purple to red to orange depending upon how they are substituted. Substitution of Tz tends to increase thermal stability, fluorescence lifetime, and fluorescence quantum yield quantum yield (QY$_{fl}$).

In some of the present embodiments, energetic pendant chemical groups (e.g. high explosive groups) are covalently bonded to a Tz ring or to a triazine ring. The presence of these chromophores enhances, or is believed to enhance, the photoactivity of the high explosive pendant chemical group without compromising its energetic performance. Absorption of visible or ultraviolet laser light by the chromophore may result in formation of radical species derived from the pendant HE bonded to the chromophore, followed by an explosion. If photoinitiation of less than an entire charge of energetic material occurs, the amount of heat produced from this partial photoinitiation may be enough to thermally initiate the remainder of the charge.

Tetrazine- and triazine-containing organic compounds. An embodiment energetic material may include a 1,2,4,5-tetrazine ring structure. Such an embodiment may have the general formula

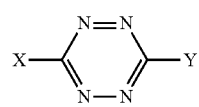

wherein X is a halide (e.g. chloride, bromide, iodide) and Y is an energetic (e.g. explosive) pendant chemical group. Such an embodiment may be prepared by reacting a precursor such as 3,6-dichloro-1,2,4,5-tetrazine (compound 1)

with one equivalent of pentaerythitol trinitrate ("PETRIN") in the presence of a base (e.g. 2,4,6-collidine) under ambient conditions in $CH_2Cl_2$ solvent. The 3,6-dibromo analog of compound 1 may also be used. The reaction is summarized in Scheme 1 below.

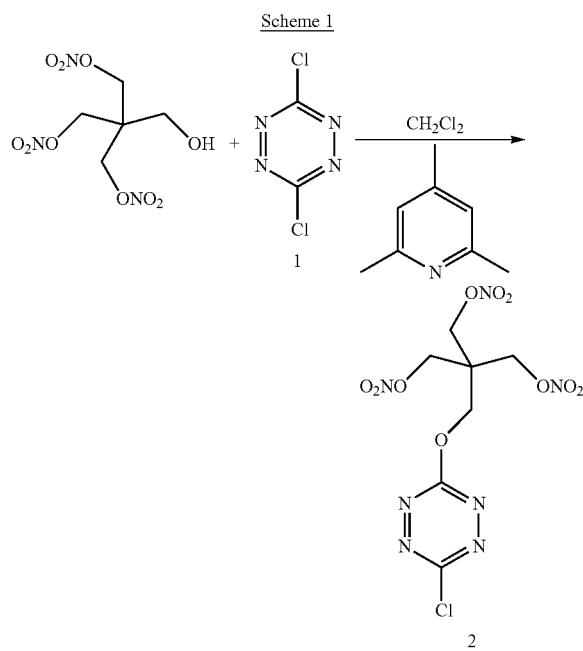

In a particular synthesis, PETRIN (2.71 grams, 10 millimoles) and 3,6-dichloro-1,2,4,5-tetrazine (1.51 grams, 10 millimoles) were added to $CH_2Cl_2$ (50 milliliters). The reaction mixture was stirred at 25° C. (i.e. 25 degrees Celsius), and 2,4,6-collidine (1.21 g, 10 millimoles) was added in portions over a 10 minute period. The reaction was monitored by thin-layer chromatography ("TLC") using $CH_2Cl_2$ as the eluent. When the reaction was complete, the reaction mixture was diluted with $CH_2Cl_2$ (50 milliliters), and the diluted reaction mixture was washed with water. The organic fraction (i.e. the $CH_2Cl_2$-containing fraction) was dried with $MgSO_4$. The mixture was filtered, concentrated by evaporating $CH_2Cl_2$, and the residue was purified by column chromatography to provide 2.66 grams of embodiment compound 2 (70% yield, melting point 77° C.). Compound 2 is a solid. The $^1H$ NMR spectrum, $^{13}C$ NMR spectrum, UV-Vis spectrum, and elemental analysis, were all consistent with the structure of compound 2, which is also referred to herein as Petrin Tetrazine Chloride or "PetrinTzCl".

The structure of compound 2 was verified by X-ray crystallography. The X-ray structure of compound 2 revealed ring structure for Tz distorted slightly from being planar and a somewhat contracted C—O—C bond angle of approximately 117 degrees compared to an angle of 123.5 degrees typically found in other alkoxytetrazines.

The pendant energetic group of compound 2 is structurally similar to the known high explosive pentaerythritol tetranitrate ("PETN"). Thus, compound 2 provides a pendant high explosive chemical group bonded covalently to a Tz ring. PETN itself cannot be photoinitiated using low energy UV or VIS laser light beam because PETN does not absorb light having such low frequencies. However, absorption of such low frequency light does occur for embodiment compound 2 (i.e. PetrinTzCl) due to absorption from the Tz chromophore, which is linked electronically to the PETN-like energetic pendant group. Thus, absorption of laser light of a suitable ultraviolet or visible wavelength by the Tz chromophore may lead to photodissociation of the energetic pendant group followed by an explosion. Modeling studies suggest that absorption of laser light of a suitable ultraviolet and/or visible wavelength by the Tz chromophore would result in bond scission to produce $NO_2$ and/or NO radical species. These types of bond scissions may result in an explosive decomposition and release of energy from compound 2. Other embodiments that are constructed with a suitably absorbing chromophore chemically bonded to an energetic pendant group are expected to photodissociate and explode in the same way or similar way after such embodiment compounds are subjected to laser light in the VIS or UV range.

Another embodiment energetic material has the structural formula

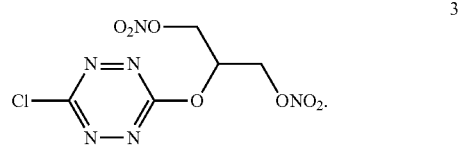

Compound 3 was synthesized by reacting 3,6-dichlo-1,2,4,5-tetrazine (compound 1) with one equivalent of 1,3-dinitroxy-2-hydroxy-propane in methylene chloride solvent under ambient conditions using 2,4,6-collidine as a base. Scheme 2 provides a summary of the synthesis of compound 3.

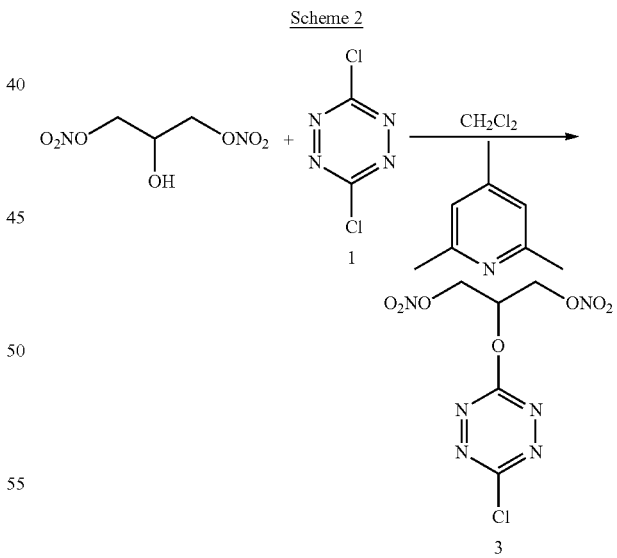

Compound 3 was liquid at liquid at room temperature, and remained a liquid after cooling to lower temperatures. Compound 2, by contrast, was a solid and in some ways (e.g. by X-ray analysis) was easier to characterize than compound 3.

The UV-VIS spectra for embodiment compounds 2 and 3 include absorption bands near 500 nm that correspond to n→π* transitions for the 1,2,4,5-tetrazine (i.e. Tz) rings. Replacement of chloride with the alkoxynitrate group had no significant effect on position of spectral bands near 500 nm, but the intense bands that appeared near 300 nm (π→π*), were red-shifted for compounds 2 and 3 compared to those of compound 1. Embodiment compounds 2 and 3 (like precursor compound 1) are fluorescent upon exposure to UV radiation at 365 nm and to shorter-wavelength UV radiation at 254 nm.

The sensitivity of compound 2 to destructive stimuli such as impact and spark and friction were similar to the sensitivity of PETN. The estimated heat of formation (using group additivity method) of compound 2 is −69 kilojoules per mole. The crystal density calculated from the X-ray data is 1.77 grams per cubic centimeter at −123° C., and 1.73 grams per cubic centimeter at 20° C. With the crystal density and an estimate of the heat of formation, we used the CHEETAH THERMOCHEMICAL CODE to calculate the explosive performance. Thus, the calculated explosive performance of compound 2 approaches that of PETN with respect to detonation velocity (7.76 kilometers/second for compound 2 versus 8.26 for PETN) and detonation pressure (25.4 GPa for compound 2 versus 33.2 GPa for PETN).

We investigated the possibility of forming a stable radical anion of compound 2. We first evaluated the electrochemical reduction of a non-energetic surrogate having the formula

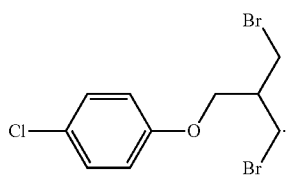 [SMILES: Clc1ccc(OCC(CBr)CBr)cc1]

This brominated analog underwent a reversible formation of a stable radical anion. We continued with compounds 2 and 3, and determined that they too underwent a reversible formation of a radical anion. We expect that compounds 2 and 3 are capable of on/off fluorescence switching through reversible oxidation/reduction chemistry. Reversible oxidation state control of compounds 2 and 3 permit the formation of stable radical anions in the presence of labile nitrate ester groups.

Compounds 4 and 5 below are other examples of embodiment monochlorinated organic energetic materials:

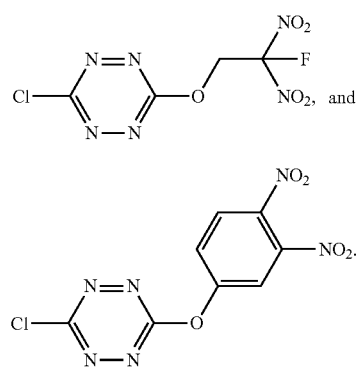

Compounds 4 and 5 may be prepared by reacting one equivalent of 3,6-dichloro-1,2,4,5-tetrazine with one equivalent of the appropriate alkoxide nucleophile.

It should be understood that embodiment energetic materials include not only monochlorotetrazines (e.g. compounds 2, 3, 4, and 5), but also their monobromo- and monoiodo-analogs, which are also photoactive or are believed to be photoactive.

Embodiment energetic materials also include di-alkoxylation products that result when 3,6-dichloro-1,2,4,5-tetrazine reacts with two equivalents of energetic alkoxide. Embodiment compound 6, having the structural formula below, was synthesized by reacting one equivalent of 3,6-dichloro-1,2,4,5-tetrazine with two equivalents of PETRIN in $CH_2Cl_2$ in the presence of 2,4,6-collidine base:

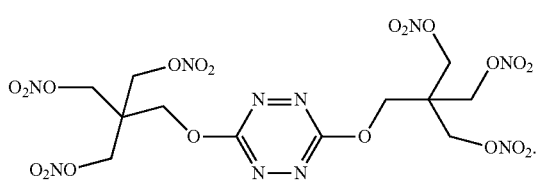

Another embodiment energetic material that is photoactive, or is believed to be photoactive, includes 3,3-dinitroazetidinyl groups covalently bonded to Tz. Such an embodiment that is photoactive, or is believed to be photoactive, may have the structural formula

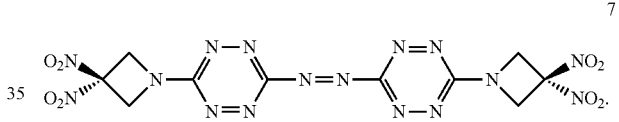

In compound 7, the Tz rings are linked to one another by a diazo (i.e. —N═N—) group, and each Tz is linked to a 3,3-dinitroazetidinyl group through the amine-type nitrogen of the 3,3-dinitroazetidinyl group. This embodiment may be prepared by nucleophilic substitution of the corresponding azo-linked (4-bromo-3,5-dimethylpyrazolyl)tetrazine with two equivalents of 3,3-dinitroazetidine. The preparation of 3,3-dinitroazetidines has been reported by Hiskey et al. "Preparation of 1-Substituted 3,3-dinitroazetidines," Journal of Energetic Materials, 1999, vol. 17, pp. 233-254, incorporated by reference herein.

Another specific embodiment of an energetic material has the structural formula

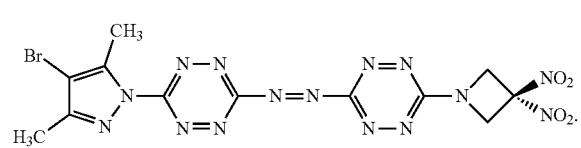

Compound 8, which is photoactive or believed to be photoactive (i.e. capable of photoinitiation using visible laser light or UV laser light) may be prepared by reacting one equivalent of 3,3-dinitroazetidine with one equivalent of compound 9.

Another embodiment energetic material is compound 9, which has the structural formula shown below:

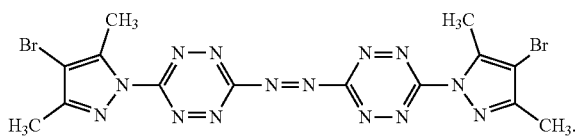

9

Embodiment compound 9, like embodiment compound 8, includes two Tz rings linked by a diazo group. Embodiments also include various N-oxides of compounds 7, 8, 9, and other N-oxides. These N-oxide derivatives may include one oxygen atom per molecule, two oxygen atoms per molecule, three oxygen atoms per molecule, four oxygen atoms per molecule, and five oxygen atoms per molecule. Thus, these N-oxides have a composition of the formula

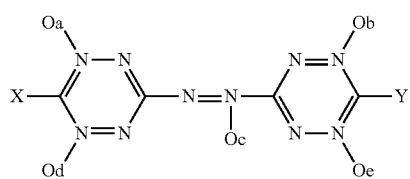

wherein the sum a+b+c+d+e equals 0, 1, 2, 3, 4, or 5, and wherein X and Y are each independently selected from —OCH$_2$C(CH$_2$ONO$_2$)$_3$, —OCH$_2$C((F)(NO$_2$)$_2$), —OCH(ONO$_2$)$_2$,

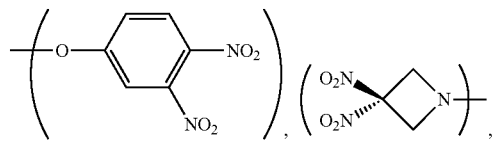

or NH$_2$. The corresponding N-oxides of 7, 8, and 9, for example, may be prepared by reacting 7, 8, or 9 with an oxidizer such as peroxytrifluoroacetic acid, hydrogen peroxide, or hypofluorous acid.

Another embodiment energetic material includes a Tz ring in which one or more of the nitrogen atoms of the Tz ring are bonded to oxygen. A particular embodiment which is photoactive or is believed to be photoactive, has the structural formula

10

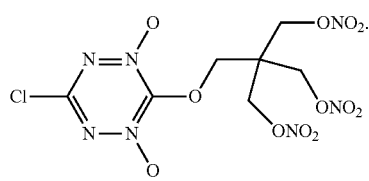

Compound 10 may be prepared by reacting embodiment compound 2 with an oxidizer such as peroxytrifluoroacetic acid, hydrogen peroxide, or hypofluorous acid. Compound 10 is photoactive or is believed to be photoactive, which means that upon exposure to laser light wavelengths from an ultraviolet and/or visible laser, the Tz chromophore of compound 10 is expected to absorb UV and/or VIS energy, resulting in photodissociation of one or more NO$_2$ groups to form radical species, and this photodissociation will eventually lead to an explosive decomposition and release of energy. Ignition using UV and/or visible light of a chosen wavelength, or in a chosen range of wavelengths, instead of heat or electricity, is believed to provide a safer means for ignition of the embodiment energetic materials than ignition by thermal means or by using electricity, because of the decreased risk of an accidental electrostatic ignition, or by some other accidental ignition.

Another embodiment energetic material includes a 1,3,5-triazine ring as the absorbing chromophore covalently bonded to an energetic pendant group. These triazine embodiments, like those derived from the Tz ring, are expected to absorb UV or VIS laser light into the 1,3,5-triazine chromophore, which will eventually resulting in photoinitiation and a release of energy, such as an explosive release of energy. Exemplary embodiments that include a 1,3,5-triazine chromophore and energetic pendant groups include those having the structural formula

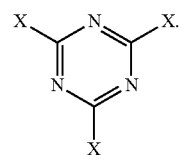

A particular embodiment is compound 11 shown below, below, in which all three of the X substituents are —OCH$_2$C(CH$_2$ONO$_2$)$_3$:

11

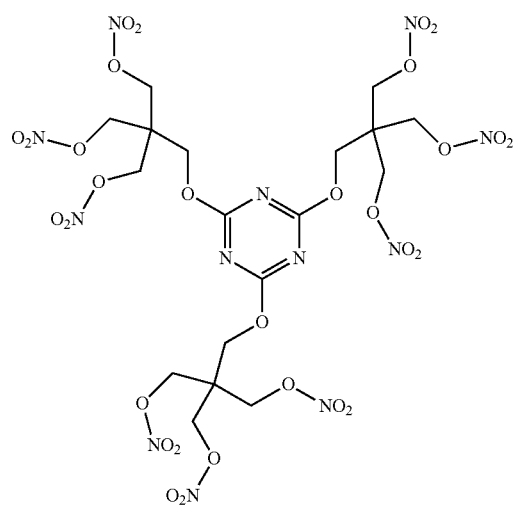

Similarly, other embodiments include those in which all three of the X substituents are: —OCH$_2$C((F)(NO$_2$)$_2$) (12) —OCH(ONO$_2$)$_2$ (13)

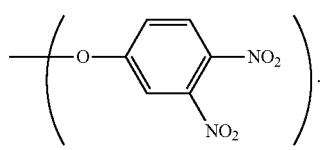

(14)

Another particular embodiment energetic material is one in which all three of the X substituents are 3,3-dinitroazetidine

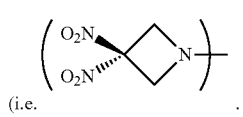

(15)

(i.e.

Embodiment compounds 11 through 15 are photoactive, or believed to be photoactive upon irradiation with relatively low energy laser light (i.e. UV and/or VIS laser light). Embodiment compounds 11, 12, 13, and 14 may be prepared by reacting one equivalent of 2,4,6-trichloro-1,3,5-triazine with three equivalents of the appropriate nucleophiles generated from their corresponding alcohols in the presence of a suitable base (see Scheme 1 for an illustration using PETRIN and Tz with 2,4,6-collidine). Embodiment compound 15 may be prepared by reacting one equivalent of 2,4,6-trichloro-1,3,5-triazine with three equivalents of 3,3-dinitroazetidine.

Embodiment energetic materials having a single triazine ring per molecule also include those prepared by reacting one equivalent of 1,3,5-trichloro-2,4,6-triazine (or 1,3,5-tribromo-2,4,6-triazine, or 1,3,5-triiodo-2,4,6-triazine) with less than three equivalents of energetic nucleophile. These include, for example, energetic materials prepared by reacting one equivalent of 1,3,5-trichloro-2,4,6-triazine with one equivalent of PETRIN in the presence of base (such as 2,4,6-collidine), which would result in a embodiment product having two halides ligand and one energetic pendant ligand per molecule of energetic material. Reaction of 1,3,5-trichloro-2,4,6-triazine with two equivalents of PETRIN and base (to convert the PETRIN to its corresponding nucleophilic alkoxide) would result in an embodiment with one halide and two energetic pendant ligands per embodiment molecule. Thus, embodiments also include energetic materials that have some energetic pendant groups but fewer than maximum number possible.

Another embodiment energetic material that is photoactive or is believed to be photoactive is a composition that includes a two 1,3,5-triazine rings linked to one another with a diazo-group. Such an embodiment may have the structural formula

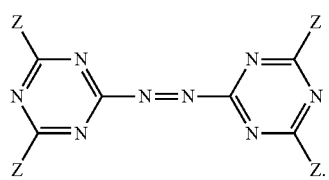

This composition includes two triazine ring structures that are linked together with an azo (i.e.

N=N—) group. In specific embodiments of this structure, each of the Z groups is are the same nitroalkoxy group selected from the following: —OCH$_2$C(CH$_2$ONO$_2$)$_3$ (16), OCH$_2$C((F)(NO$_2$)$_2$) (17), —OCH(ONO$_2$)$_2$ (18), or

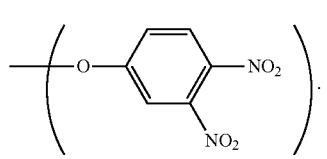

(19)

Another particular embodiment energetic material is one in which all three of the X substituents are 3,3-dinitroazetidine (i.e.

(20)

Embodiment compound 20 has the structural formula

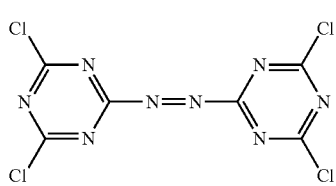

20 and may be prepared by reacting one equivalent of compound 21 below

21

With eight equivalents of 3,3-dinitroazetidine. Another embodiment has the structural formula

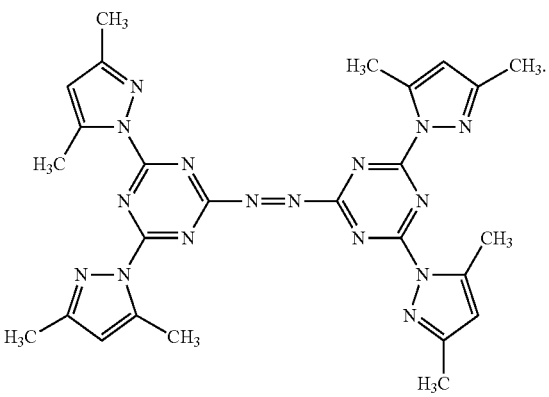

22

Compound 22 may be prepared by reacting compound 21 with four equivalents of the corresponding dimethylated pyrazole. Compound 22 by itself is not a photoactive energetic material, but could be used to prepare embodiment coordination compounds that are photoactive energetic materials (e.g. explosives).

Detailed synthetic procedures for some tetrazine-containing, triazine-containing, and other compounds follow below. The tetrazine-containing and triazine-containing compounds may be used as used as ligands for coordination compounds, at least some of which are photoactive or believed to be photoactive, upon suitable irradiation with a laser having a wavelength in the near-IR, VIS, or UV region of the spectrum. Unless otherwise noted as synthesized according to a previous publication, all of the following compounds are embodiment compounds.

Synthesis of DMPTzNH$_2$ (23). Compound 23 was synthesized according to the method described by Chavez et. al. Journal of Heterocyclic Chemistry, 1998, vol. 35, pg. 1329-1332. Compound 23 has the structure

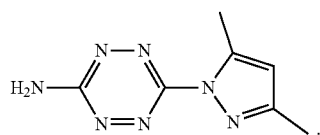

23

Synthesis of PyrTzNH$_2$ (24). Compound 24 was synthesized according to the method described by Wei et. al. Chemistry a European Journal, 2014, vol. 20, pg. 16943-16952. Compound 24 has the structure

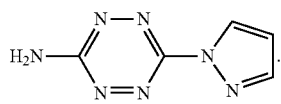

24

Synthesis of (NO$_2$Pyr)TzNH$_2$ (25). Anhydrous ammonia was bubbled through a solution of 3,6-bis(4-nitropyrazolyl)-1,2,4,5-tetrazine (1.52 g, 5.00 mmol) in MeCN (10 mL). Diethyl ether (20 mL) was added to form a red-orange precipitate. The precipitate was collected via filtration, washed with water (2×10 mL) and with MeCN (2×5 mL). The resulting orange-red powder (25, 0.811 g, 78%) was identified as (NO$_2$Pyr)TzNH$_2$. $^1$HNMR (400 mHz, d$_6$-DMSO) δ 8.49 (s, 2H, NH$_2$), 8.69 (s, 1H, pyr), 9.50 (s, 1H, pyr). Compound 25 has the structure

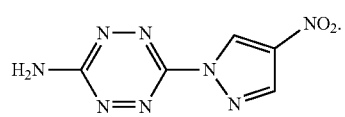

25

Synthesis of TrzTzNH$_2$ (26). Compound 26 was synthesized according to the method described by Wei et. al. Chemistry a European Journal, 2014, vol. 20, pg. 16943-16952. Compound 26 has the structure

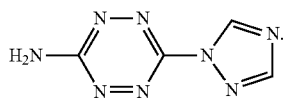

26

Synthesis of DMPTzOH (27). Compound 27 was synthesized according to the method described by Ishmetova et. al. Russian Journal of Organic Chemistry, 2009, vol. 49, pg. 1102-1107. Compound 27 has the structure

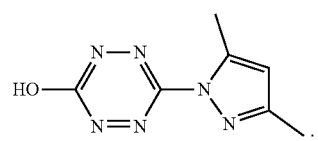

27

Synthesis of PyrTzOH (28). Solid 3,6-bis(pyrazolyl)-1,2,4,5-tetrazine (2.14 g, 10.0 mmol) was immersed in a 1.0M NaOH solution (5 mL) for 15 minutes with stirring until the solution was a uniform magenta color. The solution was neutralized with 3M HCl until an bright red-orange precipitate formed. The precipitate was collected via filtration, washed with water (2×10 mL), diethyl ether (2×5 mL) and air dried. The orange-red solid (28, 1.46 g, 89%) was identified as PyrTzOH. $^1$HNMR (400 mHz, d$_6$-DMSO) δ 6.68 (s, 1H, pyr), 7.94 (s, 1H, pyr), 8.60 (s, 1H, pyr). Compound 28 has the structure

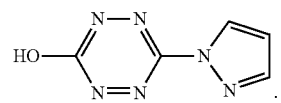

28

Synthesis of (NO$_2$Pyr)TzOH (29). Compound 29 can be synthesized in an analogous manner by immersing solid 3,6-bis(4-nitropyrazolyl)-1,2,4,5-tetrazine (1.52 g, 5.00 mmol) in 3 ml, of 1.0M NaOH for 15 minutes with stirring until the solution is a uniform magenta color. The solution can be neutralized with 3.0M HCl until an orange-red precipitate forms which can be collected via filtration, washed with water (2×10 mL), diethyl ether (2×5 mL) and air dried. Compound 29 has the structure

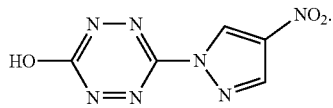

29

Synthesis of TrzTzOH (30). Compound 29 can be synthesized in an analogous manner by immersing solid 3,6-bis(1,2,4-triazolyl)-1,2,4,5-tetrazine (2.16 g, 10.00 mmol) in 5 ml, of 1.0M NaOH for 15 minutes with stirring until the solution is a uniform magenta color. The solution can be neutralized with 3.0M HCl until an orange-red precipitate forms which can be collected via filtration, washed with water (2×10 mL), diethyl ether (2×5 mL) and air dried. Compound 30 has the structure

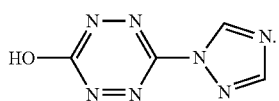

30

Synthesis of DMPTzDNAZ (31). To a solution of 3,6-bis (3,5-dimethylpyrazolyl)-1,2,4,5-tetrazine (2.72 g, 10.0 mmol) in MeCN (10 mL) was added DNAZ.HCl (1.83 g, 10.0 mmol) and triethylamine (1.11 g, 11 mmol). The resulting solution was stirred for 1 hour until the color had changed to a uniform orange-red color. Diethyl ether (20 mL) was added and the precipitate was collected via filtration. The precipitate was washed with water (3×10 mL) and diethyl ether (2×10 mL). Recrystallization of the crude material from MeCN led to isolation of DMPTzDNAZ (2, 2.50 g, 78%) as orange-red crystals. Anal. Calcd for $C_{10}H_{11}N_9O_4$: C, 37.39%, H, 3.45%, N, 39.24%. Found: C, 37.73%, H, 3.42%, N, 38.89%. $^1$HNMR (400 mHz, $d_6$-DMSO) δ 2.24 (s, 3H, $CH_3$), 2.46 (s, 3H, $CH_3$), 5.28 (s, 4H, DNAZ), 6.26 (s, 1H, pyr). $^{13}$CNMR (400 mHz, $d_6$-DMSO) δ 12.67 ($CH_3$), 13.37 ($CH_3$), 59.71 (DNAZ), 107.95 (DNAZ), 109.50 (pyr), 141.88 (pyr), 151.10 (pyr), 157.71(tz), (Tz), 162.58 (tz). Compound 31 has the structure

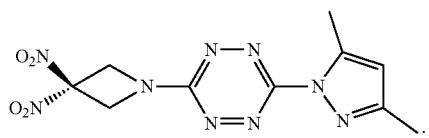

31

Synthesis of PyrTzDNAZ (32). To a solution of 3,6-bis (pyrazolyl)-1,2,4,5-tetrazine (2.14 g, 10.0 mmol) in MeCN (10 mL) was added DNAZ.HCl (1.83 g, 10.0 mmol) and triethyl amine (1.11 g, 11.0 mmol). The resulting solution was heated to reflux for 2 hours until the solution was a uniform orange-red color. The solution was cooled to room temperature and diethyl ether (20 mL) was added. The resulting precipitate was collected via filtration, washed with water (2×20 mL), diethyl ether (2×5 mL) and air dried. The orange-red powder (32, 2.17 g, 72%) was identified as PyrTzDNAZ. $^1$HNMR (400 mHz, $d_6$-DMSO) δ 5.27 (s, 4H, DNAZ), 6.73 (s, 1H, pyr), 8.01 (s, 1H, pyr), 8.72 (s, 1H, pyr). $^{13}$CNMR (400 mHz, $d_6$-DMSO) δ 60.21 (DNAZ), 108.48 (DNAZ), 109.99 (pyr), 129.88 (pyr), 144.53 (pyr), 156.98 (tz), 164.12 (tz). Compound 32 has the structure

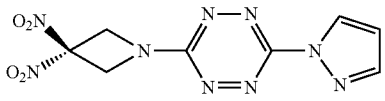

32

Synthesis of (NO$_2$Pyr)TzDNAZ (33). Compound 33 can be synthesized in an analogous manner. To a solution of 3,6-bis(4-nitropyrazole)-1,2,4,5-tetrazine (1.52 g, 5.00 mmol) in MeCN (5 mL) can be added DNAZ.HCl (0.915 g, 5.00 mmol) and triethyl amine (0.556 g, 5.50 mmol). The resulting solution can be heated to reflux for 2 hours until the solution was a uniform orange-red color. The solution can be cooled to room temperature and diethyl ether (20 mL) added. The resulting precipitate can be collected via filtration, washed with water (2×20 mL), diethyl ether (2×5 mL) and air dried to yield product. Compound 33 has the structure

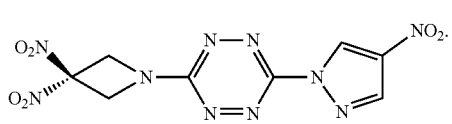

33

Synthesis of TrzTzDNAZ (34). Compound 34 can be synthesized in an analogous manner. To a solution of 3,6-bis(1,2,4-triazolyl)-1,2,4,5-tetrazine (2.16 g, 10.0 mmol) in MeCN (10 mL) can be added DNAZ.HCl (1.83 g, 10.0 mmol) and triethyl amine (1.11 g, 11.0 mmol). The resulting solution can be heated to reflux for 2 hours until the solution was a uniform orange-red color. The solution can be cooled to room temperature and diethyl ether (20 mL) added. The resulting precipitate can be collected via filtration, washed with water (2×20 mL), diethyl ether (2×5 mL) and air dried to yield product. Compound 34 has the structure

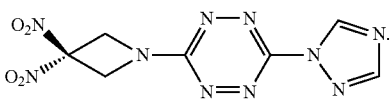

34

Synthesis of DMPTzPETriN (35). To a solution of 2 (0.385 g, 1.00 mmol) in MeCN (5 mL) was added 3,5-dimethylpyrazole (0.202 g, 2.10 mmol). The resulting solution was stirred for 2 hours and concentrated to 2 mL. Diethyl ether (10 mL) was added to precipitate an orange powder. The powder was collected via filtration, washed with water (2×5 mL), washed with diethyl ether (2×2 mL) and air dried. The resulting orange powder was identified as DMPTzPETriN. $^1$HNMR (400 mHz, $d_3$-MeCN) δ 2.31 (s, 3H, $CH_3$), 2.48 (s, 3H, $CH_3$), 4.47 (s, 2H, $CH_2$), 4.81 (s, 6H, $CH_2$), 6.25 (s, 1H, pyr). Compound 35 has the structure

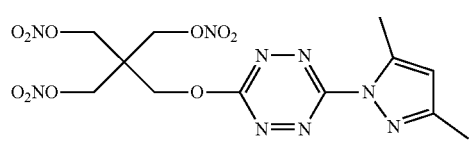

35

Synthesis of PyrTzPETriN (36). Compound 36 can be synthesized in an analogous manner.). To a solution of 2 (0.385 g, 1.00 mmol) in MeCN (5 mL) can be added pyrazole (0.143 g, 2.10 mmol). The resulting solution can be stirred for 2 hours and concentrated to 2 mL. Diethyl ether (10 mL) can be added to precipitate an orange powder. The powder can be collected via filtration, washed with water (2×5 mL), washed with diethyl ether (2×2 mL) and air dried to yield product. Compound 36 has the structure

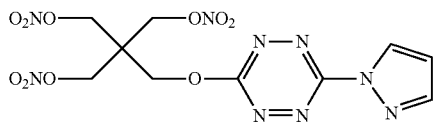

Synthesis of (NO$_2$Pyr)TzPETriN (37). Compound 37 can be synthesized in an analogous manner.). To a solution of 2 (0.385 g, 1.00 mmol) in MeCN (5 mL) can be added 4-nitropyrazole (0.237 g, 2.10 mmol). The resulting solution can be stirred for 2 hours and concentrated to 2 mL. Diethyl ether (10 mL) can be added to precipitate an orange powder. The powder can be collected via filtration, washed with water (2×5 mL), washed with diethyl ether (2×2 mL) and air dried to yield product. Compound 37 has the structure

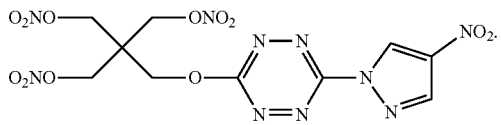

Synthesis of TrzTzPETriN (38). Compound 38 can be synthesized in an analogous manner.). To a solution of 2 (0.385 g, 1.00 mmol) in MeCN (5 mL) can be added 1,2,4-triazole (0.145 g, 2.10 mmol). The resulting solution can be stirred for 2 hours and concentrated to 2 mL. Diethyl ether (10 mL) can be added to precipitate an orange powder. The powder can be collected via filtration, washed with water (2×5 mL), washed with diethyl ether (2×2 mL) and air dried to yield product. Compound 38 has the structure

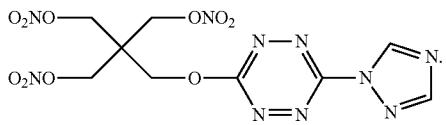

Synthesis of DMPTzTrisN (39). To a solution of 3,6-bis(3,5-dimethylpyrazolyl)-1,2,4,5,-tetrazine (2.72 g, 10.0 mmol) in MeCN (20 mL) was added 2-Amino-2-hydroxymethyl-propane-1,3-diol (1.21 g, 10.0 mmol). The solution was stirred for 2 hours at 60° C. until a dark red precipitate formed. The precipitate was collected via filtration and washed with MeCN (3×10 mL) and air dried. The dark red material was dissolved in acetic acid (5 mL) and cooled to 0° C. in an ice bath. In a separate vial 90% HNO$_3$ (3 mL) was added drop-wise to acetic anhydride (5 mL) at 0° C. The acetic anhydride nitric acid mixture was added drop-wise to the acetic acid solution at 0° C. and the resulting solution was stirred for 15 minutes. The solution was then poured into 100 mL of ice water leading to the precipitation of an orange-red material. The material was collected via filtration, washed with 1.0M NaHCO$_3$ (10 mL), washed with hexane (2×10 mL), and air dried. The resulting red-orange powder (39, 2.71 g, 63%) was identified as DMPTz-TrisN. $^1$HNMR (400 mHz, d$_6$-DMSO) δ 2.23 (s, 3H, CH$_3$), 2.46 (s, 3H, CH$_3$), 5.07 (s, 6H, CH$_2$), 6.23 (s, 1H, pyr), 9.29 (s, 1H, NH). Compound 39 has the structure

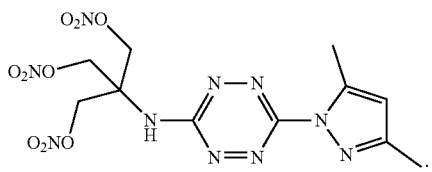

Synthesis of PyrTzTrisN (40). To a solution of 3,6-bispyrazolyl-1,2,4,5-tetrazine (2.14 g, 10.0 mmol) in DMF (10 mL) was added 2-Amino-2-hydroxymethyl-propane-1,3-diol (1.21 g, 10.0 mmol). The solution was stirred at 60° C. for 4 hours until it was a uniform dark red. The solvent was evaporated to dryness and the resulting dark red oil was sonicated in MeCN (50 mL) until a red powder formed. The red powder was collected via filtration and washed with MeCN (3×10 mL). The dark red material was dissolved in acetic acid (5 mL) and cooled to 0° C. in an ice bath. In a separate vial 90% HNO$_3$ (3 mL) was added drop-wise to acetic anhydride (5 mL) at 0° C. The acetic anhydride nitric acid mixture was added drop-wise to the acetic acid solution at 0° C. and the resulting solution was stirred for 15 minutes. The solution was then poured into 100 mL of ice water leading to the precipitation of an orange-red material. The material was collected via filtration, washed with 1.0M NaHCO$_3$ (10 mL), washed with hexane (2×10 mL), and air dried. The resulting red-orange powder (40, 1.89 g, 47%) was identified as PyrTzTrisN. $^1$HNMR (400 mHz, d$_6$-DMSO) δ 5.06 (s, 6H, CH$_2$), 6.70 (s, 1H, pyr), 7.98 (s, 1H, pyr), 8.68 (s, 1H, pyr). Compound 40 has the structure

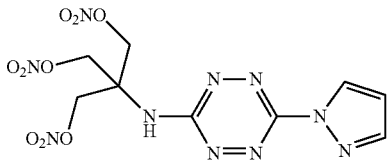

Synthesis of (NO$_2$Pyr)TzTrisN (41). Compound 41 can be synthesized in an analogous manner. To a solution of 3,6-bis(4-nitropyrazole)-1,2,4,5-tetrazine (0.304 g, 1.00 mmol) in DMF (10 mL) 2-Amino-2-hydroxymethyl-propane-1,3-diol (0.121 g, 1.00 mmol) can be added. The solution can be stirred at 60° C. for 4 hours until it is a uniform dark red. The solvent can be evaporated to dryness and the resulting dark red oil can be sonicated in MeCN (50 mL) until a red powder formed. The red powder can be collected via filtration and washed with MeCN (3×10 mL). The dark red material can be dissolved in acetic acid (5 mL) and cooled to 0° C. in an ice bath. In a separate vial 90% HNO$_3$ (3 mL) can be added drop-wise to acetic anhydride (5 mL) at 0° C. The acetic anhydride nitric acid mixture can be added drop-wise to the acetic acid solution at 0° C. and the resulting solution can be stirred for 15 minutes. The solution can be poured into 100 mL of ice water leading to the precipitation of an orange-red material. The material can be collected via filtration, washed with 1.0M NaHCO₃ (10 mL), washed with hexane (2×10 mL), and air dried. Compound 41 has the structure

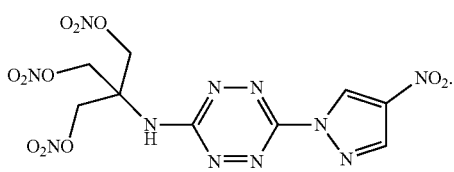

Synthesis of TrzTzTrisN (42). To a solution of 3,6-bis(1,2,4-triazole)-1,2,4,5-tetrazine (2.16 g, 10.0 mmol) in DMF (10 mL) was added 2-Amino-2-hydroxymethyl-propane-1,3-diol (1.21 g, 10.0 mmol). The solution was stirred at 60° C. for 4 hours until it was a uniform dark red. The solvent was evaporated to dryness and the resulting dark red oil was sonicated in MeCN (50 mL) until a red powder formed. The red powder was collected via filtration and washed with MeCN (3×10 mL). The dark red material was dissolved in acetic acid (5 mL) and cooled to 0° C. in an ice bath. In a separate vial 90% HNO₃ (3 mL) was added drop-wise to acetic anhydride (5 mL) at 0° C. The acetic anhydride nitric acid mixture was added drop-wise to the acetic acid solution at 0° C. and the resulting solution was stirred for 15 minutes. The solution was then poured into 100 mL of ice water leading to the precipitation of an orange-red material. The material was collected via filtration, washed with 1.0M NaHCO₃ (10 mL), washed with hexane (2×10 mL), and air dried. The resulting red-orange powder (40, 1.83 g, 41%) was identified as TrzTzTrisN. Compound 42 has the structure

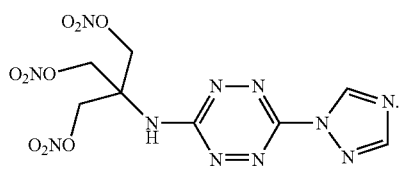

Synthesis of TriTzDMP (43). Compound 43 was synthesized according to the method described by Chavez et. al. Journal of Heterocyclic Chemistry 1998, vol. 35, pg. 1329-1332.). Compound 43 has the structure

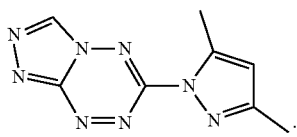

Synthesis of TriTzPyr (44). A solution of 3-hydrazino,6-pyrazolyl-1,2,4,5-tetrazine (1.50 g, 10.0 mmol) and acetic acid (0.2 ml) in triethylorthoformate (5.00 ml) was heated and stirred at 100° C. for 24 hours. The solution was cooled to room temperature and the yellow precipitate was collected via filtration, washed with cold water (50 mL) and MeCN (10 mL) to yield 44 (1.63 g, 87%) as a yellow powder. ¹HNMR (400 mHz, d₆-DMSO) 6.84 (s, 1H, pyr-CH), 8.13 (s, 1H, pyr-CH), 9.03 (s, 1H, pyr-CH), 10.06 (s, 1H, triazolo-CH) δ. ¹³CNMR (400 mHz, d₆-DMSO) 110.57 (pyr), 131.81 (pyr), 137.84 (triazolo), 145.76 (pyr), 149.22 (tz), 150.81 (tz) δ. UV-Vis spectrum (KBr pellet) 256 (1.00), 363 (0.63), 434 (0.36), 472 (0.31), 541 (0.18) nm $\lambda_{max}$ (relative intensity). ¹HNMR (400 mHz, d₆-DMSO) δ 6.84 (s, 1H, pyr), 8.13 (s, 1H, pyr), 9.03 (s, 1H, pyr), 10.07 (s, 1H, triazolo C—H). ¹³CNMR (400 mHz, d₆-DMSO) δ 111.05 (pyr), 132.29 (pyr), 138.32 (triazolo), 146.24 (pyr), 149.61 (tz), 151.46 (tz). The compound 44 has the structure

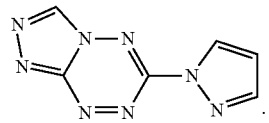

Synthesis of TriTz(NO₂Pyr) (45). A solution of 3-hydrazino,6-(4-nitropyrazolyl)-1,2,4,5-tetrazine (0.223 g, 1.00 mmol) and acetic acid (4 drops) in triethylorthoformate (2 mL) was heated and stirred at 100° C. for 24 hours. The solution was cooled to room temperature and the yellow precipitate was collected via filtration, washed with cold water (10 mL) and MeCN (5 mL) to yield 45 (0.170 g, 73%) as a yellow powder. Compound 45 has the structure

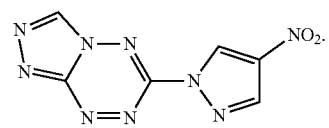

Synthesis of TriTzTrz (46). A solution of 3-hydrazino,6-(1,2,4-triazolyl)-1,2,4,5-tetrazine (0.179 g, 1.00 mmol) and acetic acid (4 drops) in triethylorthoformate (2 mL) was heated and stirred at 100° C. for 24 hours. The solution was cooled to room temperature and the yellow precipitate was collected via filtration, washed with cold water (10 mL) and MeCN (5 mL) to yield 46 (0.126 g, 67%) as a yellow powder. Compound 46 has the structure

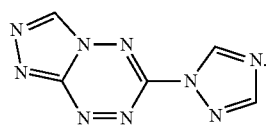

Synthesis of NH₂TriTzDMP (47). Compound 47 was synthesized according to the method described by Chavez et. al. Journal of Heterocyclic Chemistry 1998, vol. 35, pg. 1329-1332. The compound 47 has the structure

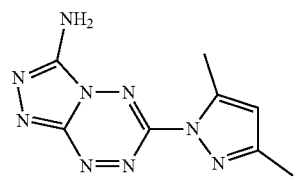

Synthesis of NH$_2$TriTzPyr (48). To a stirred solution of 3-hydrazino,6-pyrazole-1,2,4,5-tetrazine (1.50 g, 10.0 mmol) in 3M HCl (15 ml) was added cyanogen bromide (1.07 g, 10.0 mmol). The solution was stirred at room temperature for 24 hours. The dark purple precipitate was collected via filtration, washed with water (50 mL) and MeCN (10 mL) to yield 48 (1.20 g, 59%) as a dark purple powder. $^1$HNMR (400 mHz, d$_6$-DMSO) 6.76 (s, 1H, pyr-CH), 7.67 (s, 2H, NH$_2$), 8.03 (s, 1H, pyr-CH), 8.87 (s, 1H, pyr-CH) δ. $^{13}$CNMR (400 mHz, d$_6$-DMSO) 109.70(pyr), 131.29 (pyr), 144.66 (pyr), 148.11 (tz), 149.46 (tz), 149.71 (triazolo) δ. UV-Vis spectrum (KBr pellet) 244 (1.00), 286 (0.99), 386 (0.44), 543(0.20) λ$_{max}$ (relative intensity). Anal. Calcd for C$_6$H$_5$N$_9$: C, 35.47%, H, 2.48%, N, 62.05%. $^1$HNMR (400 mHz, d$_6$-DMSO) δ 6.76 (s, 1H, pyr), 7.67 (s, 2H, NH$_2$), 8.03 (s, 1H, pyr), 8.87 (s, 1H, pyr). $^{13}$CNMR (400 mHz, d$_6$-DMSO) δ 110.19 (pyr), 131.78 (pyr), 145.14 (pyr), 148.60 (tz), 149.95 (tz), 150.20 (triazolo). The compound 48 has the structure

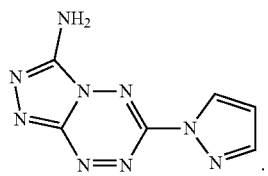

48

Synthesis of NH$_2$TriTz(NO$_2$Pyr) (49). Compound 49 can be synthesized in an analogous manner. A stirred solution of of 3-hydrazino,6-(4-nitropyrazolyl)-1,2,4,5-tetrazine (0.223 g, 1.00 mmol) and cyanogen bromide (0.107 g, 1.00 mmol) in 1.0M HCl (2 mL) can be stirred for 24 hours at room temperature. The dark purple precipitate can be collected via filtration, washed with water (5 mL), washed with MeCN (5 mL), and air dried to yield product. $^1$HNMR (400 mHz, d$_6$-DMSO) δ 8.60 (s, 1H, pyr), 9.98 (s, 1H, pyr), 10.20 (s, 1H, Triazolo C—H). Compound 49 has the structure

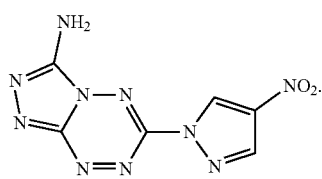

49

Synthesis of NH$_2$TriTzTrz (50). Compound 50 can be synthesized in an analogous manner. A stirred solution of of 3-hydrazino,6-(1,2,4-triazolyl)-1,2,4,5-tetrazine (0.179 g, 1.00 mmol) and cyanogen bromide (0.107 g, 1.00 mmol) in 1.0M HCl (2 mL) can be stirred for 24 hours at room temperature. The dark purple precipitate can be collected via filtration, washed with water (5 mL), washed with MeCN (5 mL), and air dried to yield product. $^1$HNMR (400 mHz, d$_6$-DMSO) δ 7.85 (s, 2H, NH$_2$), 8.50 (s, 1H, trz), 9.76 (s, 1H, trz).). Compound 50 has the structure

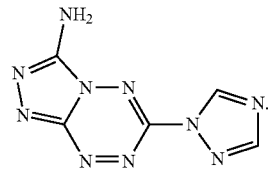

50

Synthesis of SHTriTzDMP (51). Compound 51 was synthesized according to the method described by Rusinov et. al., Russian Journal of Organic Chemistry, 1999, vol. 35, pg. 1350-1354. Compound 51 has the structure

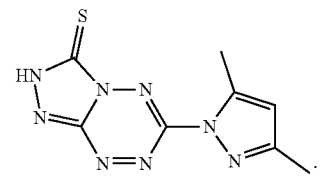

51

Synthesis of SHTriTzPyr (52). Compound 52 can be synthesized in an analogous manner. A solution of 3-hydrazino,6-pyrazole-1,2,4,5-tetrazine (0.178 g, 1.00 mmol) and carbon disulfide (0.076 g, 1.00 mmol) in acetic acid (2 mL) can be stirred for 24 hours at 40° C. The resulting H$_2$S formed in this reaction can be quenched by bubbling the off gasses through a solution of 10% hydrogen peroxide. The reaction mixture can be poured into water (10 mL) and the resulting precipitate collected by filtration, washed with water (2×5 mL), washed with diethyl ether (2×5 mL) and air dried to yield product. Compound 52 has the structure

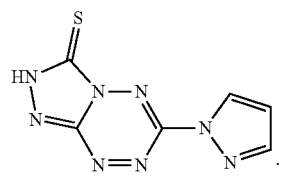

52

Synthesis of SHTriTz(NO$_2$Pyr) (53). Compound 53 can be synthesized in an analogous manner. A solution of 3-hydrazino,6-(4-nitropyrazole)-1,2,4,5-tetrazine (0.223 g, 1.00 mmol) and carbon disulfide (0.076 g, 1.00 mmol) in acetic acid (2 mL) can be stirred for 24 hours at 40° C. The resulting H$_2$S formed in this reaction can be quenched by bubbling the off gasses through a solution of 10% hydrogen peroxide. The reaction mixture can be poured into water (10 mL) and the resulting precipitate collected by filtration, washed with water (2×5 mL), washed with diethyl ether (2×5 mL) and air dried to yield product. Compound 53 has the structure

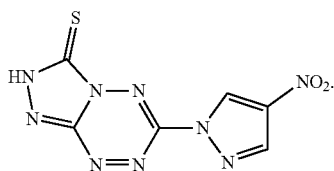

53

Synthesis of SHTriTzTrz (54). Compound 54 can be synthesized in an analogous manner. A solution of 3-hydrazino,6-(1,2,4-triazolyl)-1,2,4,5-tetrazine (0.179 g, 1.00 mmol) and carbon disulfide (0.076 g, 1.00 mmol) in acetic acid (2 mL) can be stirred for 24 hours at 40° C. The resulting $H_2S$ formed in this reaction can be quenched by bubbling the off gasses through a solution of 10% hydrogen peroxide. The reaction mixture can be poured into water (10 mL) and the resulting precipitate collected by filtration, washed with water (2×5 mL), washed with diethyl ether (2×5 mL) and air dried to yield product. Compound 54 has the structure

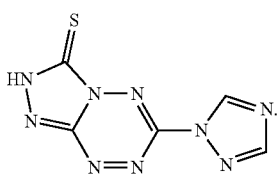

54

Photochemistry of PETN, precursor compound 1, and energetic embodiment compound 2 ("PetrinTzCl"). Pentaerythritol tetranitrate ("PETN") is a high explosive ("HE") that initiates with traditional shock and thermal stimuli, but is not photoinitiated using VIS or UV laser light.

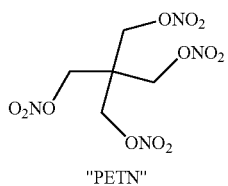

"PETN"

By contrast, embodiment compound 2 exhibits a photochemical quantum yield ($QY_{PC}$) at 532 nm that is not evident with PETN.

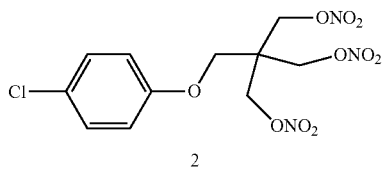

2

The $QY_{PC}$ is also enhanced by an increase in the intensity of irradiation. We therefore expect that compound 2 will photodissociate when exposed to a suitably intense beam of laser light at a wavelength or wavelengths in VIS and/or UV region of the electromagnetic spectrum. The major photoproducts are expected to be $N_2$, Cl—CN, and Petrin-CN.

The excitation mechanism is believed to involve sequential photon absorption. Dynamic simulations suggest that the relaxation mechanism leading to the observed photochemistry in compound 2 is due to vibrational excitation during internal conversion. The single photon stability and intensity dependence of compound 2 suggests that compound 2 could be stable in ambient lighting, yet could be photoinitiated using short-pulsed lasers.

UV absorption spectra of compound 1, embodiment compound 2, and PETN were obtained using an AGILENT TECHNOLOGIES 8453 UV-Vis spectroscopy system. Each compound was ground with potassium bromide (KBr: Fisher Infrared grade) and pressed into 7 mm diameter pellets using an International Crystal Laboratories Port-A-Press. Pellets were mounted to an Al mount with a 3-mm diameter hole, where the most optically clear region was selected for investigation. Concentrations were chosen such that a maximum 532 nm absorption was <0.5 and all pellets used in the intensity dependent measurements were within ±5% of each other in peak absorbance. The number of molecules in a 3 mm diameter pellet for compound 1 was approximately $5 \times 10^{17}$ molecules; for compound 2 the number was approximately $5.3 \times 10^{16}$ molecules, and for PETN the number was approximately $2.3 \times 10^{17}$ molecules.

The fluorescence QY ("$QY_{fl}$") for embodiment compound 2 was determined using the Rhodamine 6G perchlorate (ACROS ORGANICS laser grade 99.0% pure) in ethanol standard of $\Phi_f$=0.95. A 10 mm quartz cuvette was filled with the respective material. The material was excited with a continuous wave 405 nm, 89.8 mW (±0.2 mW) diode laser. Emission spectra were obtained using a focusing lens attached to a fiber connected to a spectrometer (Ocean Optics USB 2000+). The 405 nm excitation laser was blocked from the collected emission spectra with a 405 nm notch filter. A $1.4 \times 10^{-4}$M solution of compound 2 in acetone (ACROS spectroscopic grade) was investigated to keep absorption <0.1. The photochemical quantum yield, $QY_{PC}$, for continuous wave (CW) and pulsed 532 nm laser light was measured for the three materials. Molecular reactivity/photodegradation was measured via difference Fourier transform infrared (FTIR) spectra before and after photoirradiation. An FT-IR spectrometer (THERMOSCIENTIFIC NICOLET iS 5) was modified to allow in situ CW or pulsed 532 nm irradiation and IR spectroscopy. A frequency-doubled diode pumped solid state (CNI model MGL-III-532) 532 nm CW laser and a Continuum Minilite (Q-switched, 5.7 ns FWHM, ≤15 Hz pulsed 532 nm) laser were utilized to irradiate the materials. Pulsed 532 nm power was adjusted through a waveplate and polarizer. Both lasers were sent through a telescoping lens system to optimize the beam profile to a Gaussian configuration for consistent intensity/power irradiation with 2 mm FWHM. A Stanford Research Systems residual gas analyzer (RGA-200) quadrupole mass spectrometer was employed to measure the gaseous photoproducts from each of compound 1, compound 2, and PETN under CW (74 mW average power) and pulsed (64 mW average power, 15 Hz) 532 nm laser irradiation. Sample pellets (7-mm diameter) were prepared as described above for UV-Vis spectroscopy. The pellets were placed within a vacuum cell. Samples were evacuated to <$10^{-6}$ Torr using a VARIAN turbo-V70 pump and mass spectra were obtained before and during laser irradiation, while continuously pumping the cell. Continuous pumping provided the highest level of background stability. Mass spectra from 1-200 mass/charge ratio were acquired every 40 seconds, with 3 scans averaged. Mass spectra were compared to the NIST Chemistry WebBook.

Computational Methods: Linear and Nonlinear Optical Spectra. Quantum chemical calculations of optical spectra were performed with Gaussian 03 and 09 software packages. Optimized ground state geometries were calculated at the HF/6-31+G* level and vertical excitation energies were calculated using time-dependent density functional theory (TD-DFT) at the B3LYP/6-31G* level. Even though HF geometries are expected to be less accurate compared to DFT geometries obtained with some functionals with respect to experimental data, a combination of HF geometries with TD-B3LYP approach produces consistent results for calculations of linear and non-linear optical spectra across the wide range of molecular sizes. Transition dipoles between the first and higher lying excited states were calculated using the Collective Electronic Oscillator (CEO) formalism.

To simulate the sequential absorption spectrum from the first excited state to higher excited states, the transition energies were broadened by a Gaussian function with full width at half maximum of 0.05 eV. The resulting peaks were then weighted by the oscillator strengths calculated from the transition dipoles and summed, after which the total spectrum was normalized. A similar method was used to simulate the absorption spectrum for ground to excited state transitions using the corresponding oscillator strengths. The non-linear two-photon absorption (TPA) cross section was also calculated in units of Goeppert-Meyers (GMs).

Nonadiabatic Excited State Molecular Dynamics. The excited state dynamics of compound 1 and embodiment compound 2 were explored using a previously developed nonadiabatic excited state molecular dynamics (NA-ESMD) framework. Briefly, the NA-ESMD approach combines the Fewest Switches Surface Hopping (FSSH) method with semiempirical Austin Model 1 (AM1) and Configuration Interaction Singles (CIS) description of the excited states with on the fly calculation of the electronic energies, gradients and nonadiabatic coupling vectors for the excited states. The electronic degrees of freedom are treated quantum mechanically, and the nuclear motions are treated classically. The probability for a quantum transition to another excited state depends on the strength of the nonadiabatic couplings calculated at each integration step along the trajectory. We used this approach to model the relaxation of a photoexcited wave packet from the excited state. First, we ran molecular dynamics in the ground electronic state starting from the ground state optimized geometry for 300 picoseconds (ps) with a time step of $\delta t=0.5$ femtoseconds ("fs"). The system was then heated and allowed to equilibrate to a final temperature of 300 K during the first 10 picoseconds ("ps") using the Langevin thermostat with a friction coefficient of 20.0 $ps^{-1}$. From the remaining 290 ps, we collected 190 configurations for compound 1 and 290 configurations for embodiment compound 2 sampled at 1 ps intervals, which provided initial geometries and momenta for excited state simulations. Twenty compound 1 and twenty five compound 2 lowest energy electronic excited states and their oscillator strengths were then calculated for every configuration to determine energetic positions of the sequential two-photon state (located approximately 2.5 eV above the lowest energy excited $S_1$ state). The initial excited state was chosen according to a Frank-Condon window defined as $g_\alpha=\exp[-T^2(E_{laser}-\Omega_\alpha)^2]$ where $E_{laser}$ represented the excitation energy and $\Omega_\alpha$ represented the computed energy of state $\alpha$ (expressed in units of $fs^{-1}$). The laser temporal profile was Gaussian $f(t)=\exp(-t^2/2T^2)$, $T=42.5$ fs corresponding to a FWHM of 100 fs. The initial excitation was selected according to the relative values of $g_\alpha$ weighted by the oscillator strengths of each state. The NA-ESMD simulations were then started allowing internal conversion ("IC") through coupled Born-Oppenheimer surfaces to be followed as the system returned to $S_1$. The swarm of independent trajectories was propagated via energy conserving Newtonian dynamics for 1 picosecond (compound 1) and 4 ps (compound 2) using a classical time step of $\delta t=0.1$ femtoseconds and 3 quantum steps per classical step. The quantum time step was further reduced by a factor of 40 to locate trivial unavoided crossings and the electronic decoherence was included by resetting the quantum coefficients following every attempted hop.

FIG. 1 shows UV-VIS absorbance spectra for PETN, compound 1 (tetrazine dichloride), and embodiment compound 2 (Petrin tetrazine chloride). PETN is a white compound. Energetic compound 2, which includes a Petrin ligand, has a bright pink/orange color. This difference in color between compounds 1 and 2 is reflected by an enhanced absorption at wavelengths of approximately 325 nanometer ("nm") and 500 nm in the the absorption spectra as shown in FIG. 1. The continuously increasing absorption with decreasing wavelength in PETN is due to scattering in the KBr pellet; scattering has been partially subtracted out by setting the absorption at 600 nm equal to zero. The n-$\pi^*$ transition in compound 2 has substantial absorption at 532 nm permitting excitation at an easily obtained commercial laser wavelength.

The number of molecules reacted per photon absorbed for continuous wave ("CW") and pulsed 532 nm laser irradiation was measured for PETN, compound 1 and embodiment compound 2. The $QY_{PC}$ was directly calculated from the number of molecules irradiated within the 3-mm sample, the laser irradiance, and determination of the rate of molecular reactivity/photodegradation resulting from irradiation. The molecular reactivity was acquired via difference Fourier transform infrared ("FT-IR") spectra taken before and after photoirradiation at regular intervals.

Figure 2:
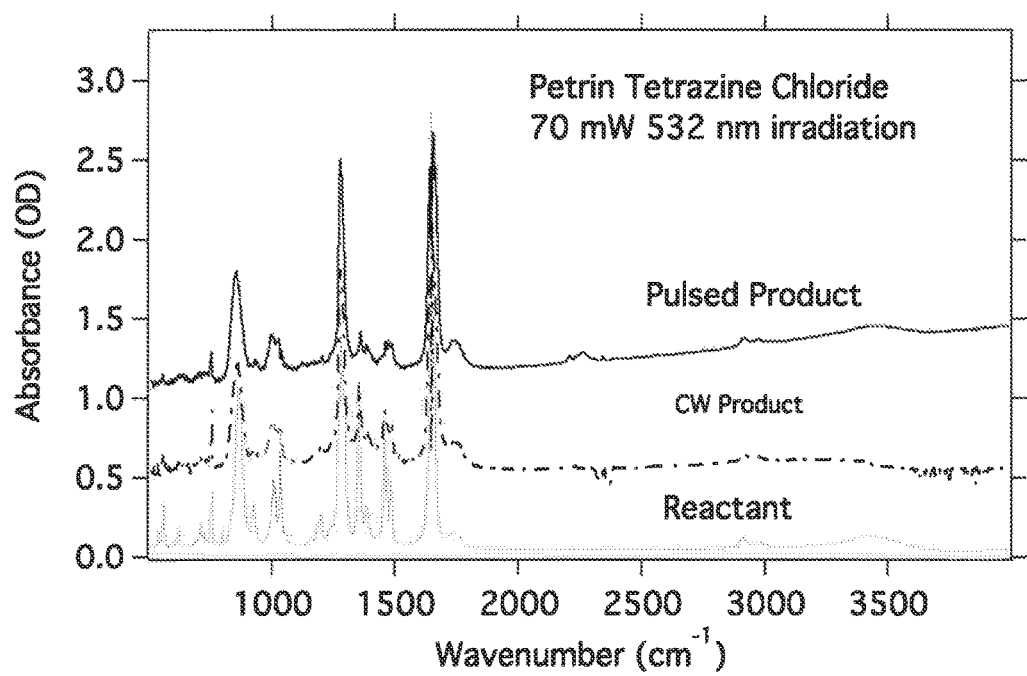
FIG. 2 shows Fourier Transform Infrared ("FT-IR") spectra of embodiment compound 2 before and after 532 nm irradiation with continuous wave ("CW", 70 milliwatt ("mW")) and pulsed (70 mW, 15 Hz) laser light. The bottom trace is a spectrum of embodiment compound 2 (PetrinTzCl, bottom trace) before irradiation. The middle trace is a spectrum of photoproduct(s) after irradiating compound 2 with a 70 milliwatt ("mW"), continuous wave ("CW") light source at a wavelength of 532 nm. The top trace is a spectrum of photoproduct(s) after irradiating compound 2 with a 70 mW, pulsed light source (70 mW, 15 Hz).

FIG. 2 shows FT-IR spectra of embodiment compound 2 before and after 532 nm irradiation with continuous wave ("CW", 70 milliwatt ("mW")) and pulsed (70 mW, 15 Hz) laser light. The bottom trace is a spectrum of embodiment compound 2 (PetrinTzCl, bottom trace) before irradiation. The middle trace is a spectrum of photoproduct(s) after irradiating compound 2 with a 70 milliwatt ("mW") continuous wave ("CW") light source at a wavelength of 532 nm. The top trace is a spectrum of photoproduct(s) after irradiating compound 2 with a 70 milliwatt pulsed light source (70 mW, 15 Hz).

Difference spectra (i.e. spectra from photoproducts subtracted from spectra of reactants) show the material vibrational changes that occurred due to photochemistry. Photoproduct vibrational spectra were determined by adding back a fractional amount, a, of the reactant spectra to the difference spectra such that negative peaks were removed. The concentration of initial material that had reacted, a, was determined in an automated process by minimizing the magnitude of the autocorrelation peak between the final product spectrum and the initial spectrum. If the trial a was too small, negative peaks would be apparent in the product spectrum and there would be a negative autocorrelation peak. If α was too large, the autocorrelation peak would become positive. We determined the fraction reacted and the final product spectrum according to equation 1 below, i.e. by calculating the magnitude of the autocorrelation as a function of α in steps of 0.25% material reacted.

$$\text{Products}=\text{difference spectra}+\alpha*\text{Reactants} \quad (1)$$

FIG. 2 shows the reactant, CW product and pulsed product spectra for embodiment compound 2. Specific peaks detailing the photochemistry are discussed below, but first we used the spectra to determine the fraction of material that reacts under different irradiation conditions.

To test the effect of intensity, new pellets of PETN, compound 1, and embodiment compound 2 were subjected to various pulsed laser irradiances and compared to CW irradiation. Fraction of material reacted and product spectra were determined for each incremental increase in irradiation. Compound 1 and embodiment compound 2 each displays nonlinear/multiphoton intensity dependence with 532 nm irradiation. There was no measurable photoreaction of PETN following 10,000, 1.8 mJ, 5.7 ns pulses of 532 nm irradiation, due to its lack of absorption at that wavelength. Embodiment compound 2 presented a 19-fold increase in QY from $1.3 \times 10^{-4}$ (CW) to $2.5 \times 10^{-3}$ (pulsed) whilst compound 1 revealed a 54-fold increase from $7.1 \times 10^{-3}$ (CW) to 0.39 (pulsed). As FIG. 1 shows, light at a wavelength of 532 nm excites the first optically active electronic state resonantly, allowing sequential absorption of a second photon prior to relaxation with increasing probability as the intensity increases. This higher excited state appears to have a much greater photochemical reactivity, which is not surprising considering the substantial increase in excess energy following absorption of two photons.

Figure 3:
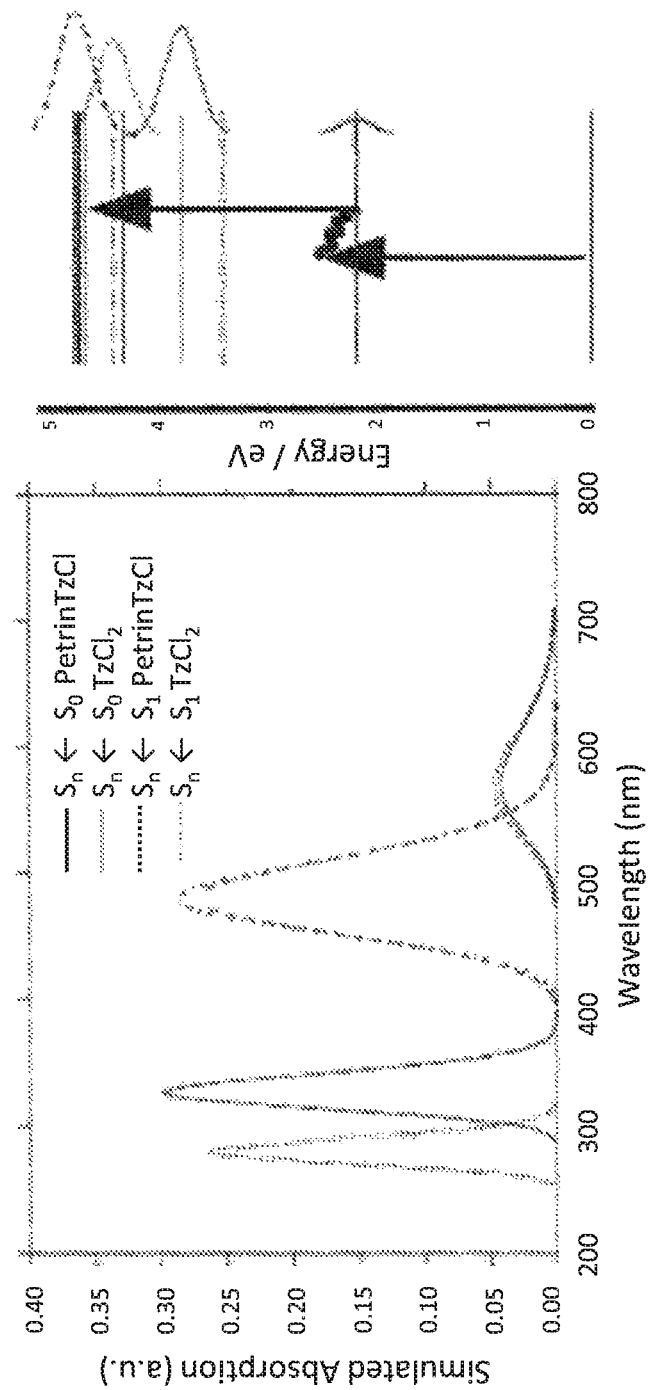
FIG. 3a shows simulated ground to excited state, and excited state to excited state, absorption spectra for compound 1 and for embodiment compound 2.
FIG. 3b shows and excitation energy diagram for compound 1 and for compound 2.

To determine the nature of the two photon process, theoretical calculations were performed to differentiate between sequential absorption and nonlinear TPA. The standard absorption spectrum from the ground to excited state is calculated to be close 570 nm, with an error estimated to be approximately 40 nm likely caused by dielectric environmental effects in experimental spectra that are not accounted for in theory. The calculated TPA cross section is relatively small with a maximum of less than 2 GMs for embodiment compound 2 and below numerical precision for compound 1. Under the laser conditions of the experiment, the TPA was approximately 6 orders of magnitude smaller than the one photon absorption, and can be neglected. The sequential absorption from the first excited state has significant absorption probability, which intersects with the ground-to-excited state absorption. The relevant spectra for one-photon absorption and sequential absorption from the first excited state are shown in FIG. 3a. The highest sequential absorption probability is close to the 532 nm range and likely has a similar error (~40 nm) as the calculated absorption probability from the ground state. This sequential absorption can lead to a total excess electronic energy of 4.5-5 eV above the ground electronic state, corresponding to the 6-8$^{th}$ B3LYP singlet excited states. These states cannot be optically excited by one-photon absorption (FIG. 3b), but can be optically excited by sequential absorption from the first excited electronic state (FIG. 3b). These states do not have significant two-photon absorption cross-section. Sequential two-photon absorption appears to be the primary method of excitation to higher energy excited states in these experiments.

Additional analysis of the reactant and product spectra of PETN, compound 1, and embodiment compound 2 were performed. PETN was not photoreactive at 532 nm and therefore had no product spectra. Compound 1 presented negligible product spectra in the infrared that could be the result of CW irradiation induced photochemistry. The product (CW or pulsed) spectra of embodiment compound 2 were similar to the reactant vibrational spectra. Distinctions between the two include an overall decrease in peak intensity with some peak broadening. Specifically, vibrations in embodiment compound 2 associated with the $NO_2$ stretch (1695 cm$^{-1}$), CH scissors (1483 cm$^{-1}$), $CH_2$ wag (1387 cm$^{-1}$), and O—N stretch (862) all remained after irradiation. There is also evidence of the Tz ring contribution at approximately 925 cm$^{-1}$ and 1198 cm$^{-1}$, although the 925 cm$^{-1}$ vibration shifts slightly to 930 cm$^{-1}$ in the product spectra.

A vibrational peak at 1352 cm$^{-1}$ is present in compound 2 but not in spectra for either PETN or compound 1. This vibrational peak may be associated with the C—O—C bonds that connect Tz to the energetic pendant Petrin group. The 1352 cm$^{-1}$ vibrational peak decreases significantly in both CW and pulsed product spectra; the larger decrease of the two was observed in the CW product spectra.

New vibrational peaks appeared in the pulsed product spectra of compound 1 (2209 cm$^{-1}$), and also in the CW (2340 cm$^{-1}$) and pulsed (2209, 2250 and 2340 cm$^{-1}$) product spectra of compound 2. The 2209 cm$^{-1}$ peak may be due to a Cl-CN vibration. The broad 2250 cm$^{-1}$ peak may be due to Petrin-CN. A sharp 2340 cm$^{-1}$ peak was observed in both CW and pulsed compound 2 but not in compound 1. This peak may be due to an isocyanate or nitrile species, or to a complex with $N_2$ products.

Peaks in the product spectra indicate the presence of a CN triple bond, which is consistent with chemistry localized on the Tz of embodiment compound 2 ("PetrinTzCl"). Mass spectra of the gaseous photoproducts from compound 1 and embodiment compound 2 after laser irradiation at 532 nm were obtained. Energy transfer leading to photodecomposition of the energetic pendant group of embodiment compound 2 lead to $NO_2$ and larger fragment gaseous photoproducts derived from the pendant group with prominent peaks expected at m/z of 46 and 76.

Thus, embodiment compound 2 undergoes decomposition through the Tz ring, while the energetic pendant group is largely intact. This decomposition occurs at a lower photochemical quantum yield than the analogous decomposition in compound 1. The mechanism for this selective decomposition is a complex interplay of photoinduced pathways of internal conversion (IC) and/or intermolecular vibrational relaxation (IVR).

Our theoretical and experimental results suggest that photochemical decomposition of compound 1 and embodiment compound 2 can occur through sequential two-photon absorption to higher lying excited states and rapid IC to the $S_1$ excited state.

While PETN is not optically active in the visible region, coupling the energetic Tz chromophore to a PETN-like pendant group increases the photoactivity of the pendant group at the commonly available laser wavelength of 532 nm. This derivatized material, PetrinTzCl (embodiment compound 2) follows a multiphoton intensity-dependent 532 nm absorption that increases its photon quantum yield by 19-fold at the maximum intensity employed here, which is easily achieved by small nanosecond lasers. The high intensity photodecomposition primarily follows a Tz ring photodecomposition, which yields Cl—CN, Petrin-CN and $N_2$. Theoretical calculations on two-photon absorption confirm the resonant cascaded process is dominant at the intensities employed. The two-photon cascaded absorption is highly selective allowing the system to access electronic states that are otherwise inaccessible through linear one-photon absorption. NA-ESMD calculations suggest that reaction occurs due to ultrafast (approximately 100-200 fs) internal conversion where the excess electronic energy from the highly excited sequential two-photon state is dissipated into vibrational kinetic energy as the system relaxes to $S_1$. The PETN-like pendant group also stabilizes the tetrazine to ambient light while maintaining the potential to initiate photochemistry through multiphoton processes with intense pulsed light. These insights are suggestive for design of the future generation of functional photoactive high explosives initiated optically.

PETN (pentaerythritol tetranitrate), a conventional high explosive, has been synthetically coupled to an optically active tetrazine chromophore, increasing its photoactivity at a commonly available laser wavelength of 532 nm. This material, PetrinTzCl (pentaerythritol trinitrate chlorotetrazine, embodiment compound 2), exhibits a sequential two photon intensity dependent 532 nm absorption which increases its photon quantum yield by 19-fold at the maximum intensity employed herein. The high intensity photodecomposition primarily follows a Tz ring photodecomposition, which yields Cl-CN, Petrin-CN and $N_2$. Theoretical calculations confirm the resonant cascaded process is dominant at the experimental intensities employed. Calculations also suggest that reaction occurs due to internal conversion.

Energetic coordination compounds. Embodiments also include energetic coordination compounds. Many of these are photoactive, or believed to be photoactive, upon irradiation with a laser with a wavelength or wavelengths in the near-IR, VIS, and/or UV region suitable for photoinitiation.

Elemental analyses of these coordination compounds were performed by Atlantic Microlab, Inc. of Norcross, Ga. or by using a Perkin Elmer series II 2400 CHNS/O analyzer. $^1$HNMR spectra were recorded at ambient temperature using a BRUKER AVANCE 400 MHz spectrometer. Chemical shifts (δ) were referenced to the residual solvent signal. Electrochemical measurements were recorded under a dinitrogen atmosphere using a CHI Electrochemical Analyzer, a glassy carbon working electrode, a Pt wire auxiliary electrode, and a Ag/AgNO$_3$ nonaqueous reference electrode. Reported potentials are all referenced to the Fc/Fc$^+$ couple and were determined using ferrocene as an internal standard. Unless noted otherwise, UV-vis spectra were recorded in acetonitrile (MeCN) solutions using an HP 8453 AGILENT UV-vis spectrometer. X-ray diffraction studies were carried out on a BRUKER APEX II equipped with a CCD area detector or on a RIGAKU R-axis IV with an imaging plate detector. Measurements were carried out at −173° C. using Mo Kα 0.71073 radiation. Crystals were mounted on a KAPTAN loop with PARATONE-N oil. Initial lattice parameters were obtained from a least-squared analysis of more than 100 centered reflections; these parameters were later refined against all data. Data were integrated and corrected for Lorentz polarization effects using SAINT and were corrected for absorption effects using SADABS 2.3. Space group assignments were based upon systematic absences, E statistics, and successful refinement of the structures. Structures were solved by direct methods with the aid of successive difference Fourier maps and were refined against all data using the SHELXTL 5.0 software package. Thermal parameters for all non-hydrogen atoms were refined anisotropically. Hydrogen atoms, where added, were assigned to ideal positions and refined using a riding model with an isotropic thermal parameter 1.2 times that of the attached carbon atom (1.5 times for methyl hydrogens). Deuterated solvents were purchased from CAMBRIDGE ISOTOPES LABORATORES, INC. and used without purification.

Compound 23 (3-amino-6-(3,5-dimethylpyrazole)tetrazine, vide infra, was synthesized according to a literature procedure. All other reagents were purchased from commercial vendors and used without further purification.

Energetic coordination compounds include a cationic coordination complex having a central metal ion bonded to energetic ligands. A variety of such materials were synthesized and characterized. Embodiments may include a transition metal (e.g. Fe, Cu) bonded to an energetic ligand.

Coordination complexes are identified herein using Roman numerals. An exemplary embodiment photoactive coordination compound includes a cationic Fe(II)L$_3$ coordination complex and associated counterion(s). The ligand L may be, for example, compound 23 ("NH$_2$TzDMP"), or compound 31, or compound 39, whose structures are shown below. Compounds 31 and 39 are themselves energetic materials, while compound 23, itself, is not.

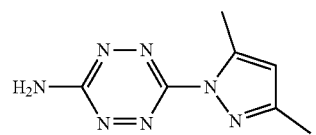

23

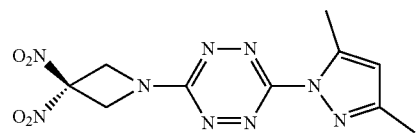

31

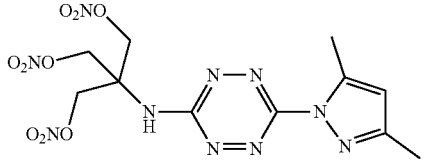

39

These coordination complexes are octahedral complexes with a central transition metal bonded to atoms from the ligands. The Fe(II)L$_3$ coordination complexes were prepared by reacting a suitable Fe-containing precursor complex with three equivalents of ligand in a suitable solvent (e.g. acetonitrile) at a suitable temperature (e.g. at room temperature)

Suitable Fe-containing precursor complexes include Fe(II) or Fe(III) and labile ligands (e.g. H$_2$O) that may be exchanged with energetic ligands. The counterions are typically those contributed by the Fe-containing precursor. The negative charges from the counterions balance the positive charges of the cationic complexes. Exemplary counterions include, but are not limited to, the complex ions tetrafluoroborate (BF$_4^{-1}$), nitrate (NO$_3^{-1}$), perchlorate (ClOhd 4$^{-1}$), sulfate (SO$_4^{-2}$), phosphate (PO$_4^{3-}$), carbonate (CO$_3^{2-}$), and the like.

An exemplary embodiment coordination compound is [(DMPTzNH$_2$)$_3$Fe][BF$_4$]$_2$, which was prepared by reaction of hexaaquoiron(II)tetrafluoroborate (Fe(H$_2$O)$_6$(BF$_4$)$_2$) with compound 23 in acetonitrile solvent at room temperature. Scheme 3 below summarizes the reactions of Fe precursors with compounds 23 to 42. It should be noted that cationic complexes with ligands 23-30 and ligands 43-54 are not energetic themselves, but lead to explosive compounds when paired with oxidizing anions such as perchlorate (ClO$_4^{-1}$). By contrast, ligands 31-42 are energetic themselves and do not need oxidizing anions to form embodiment explosive complexes.

Scheme 3

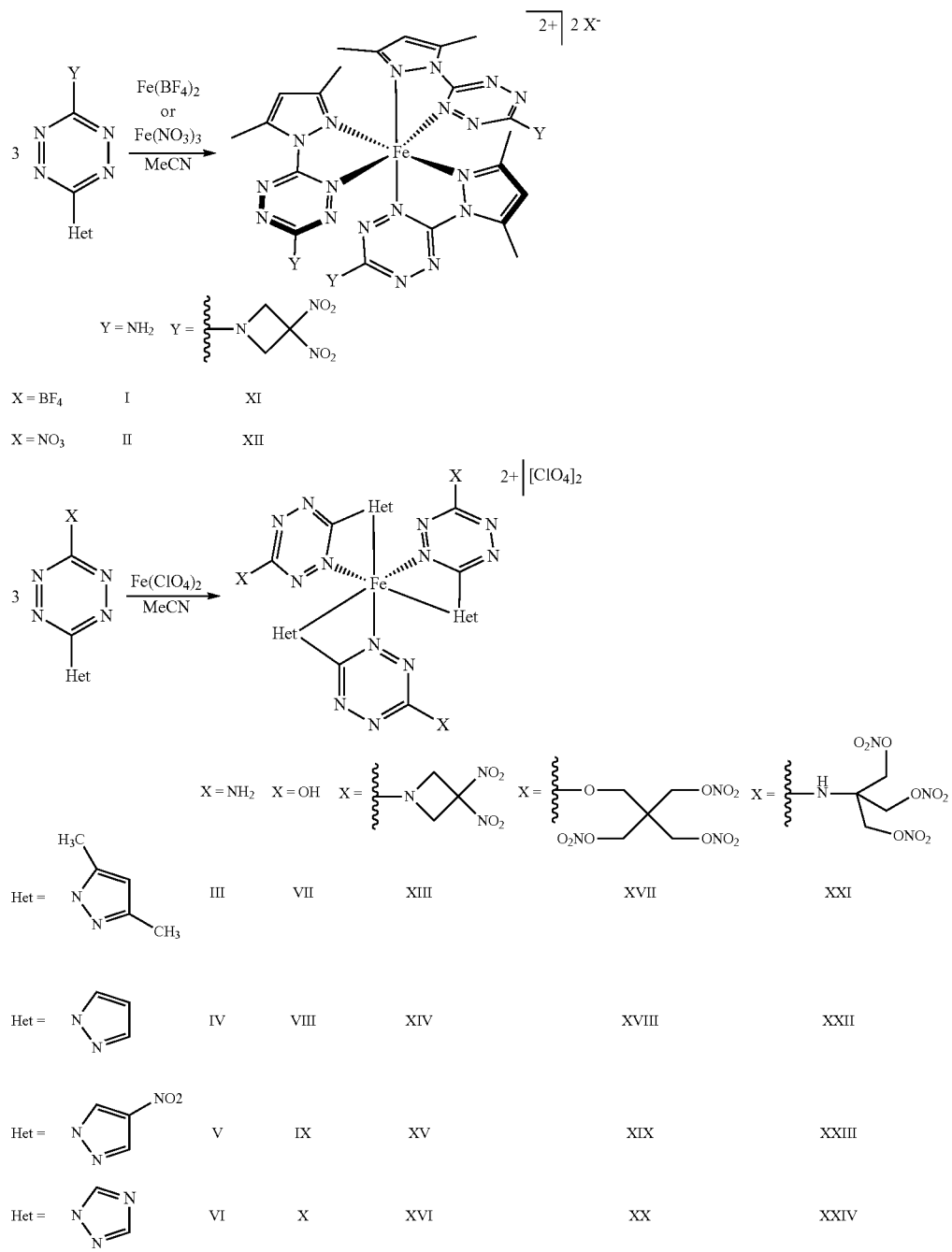

The reaction of hexaaquoiron(II)tetrafluoroborate (Fe(H$_2$O)$_6$(BF$_4$)$_2$) with compound 23 in acetonitrile solvent at room temperature rapidly produced a blue colored solution from which embodiment coordination compound I [(DMPTzNH$_2$)$_3$Fe][BF$_4$]$_2$ was isolated in 82% yield. Similarly, (Fe(H$_2$O)$_6$(NO$_3$)$_3$) reacted with compound 23 in acetonitrile solvent at room temperature to afford embodiment compound II. Reaction of (Fe(H$_2$O)$_6$(BF$_4$)$_2$) with compound 31 in acetonitrile solvent at room temperature gave embodiment compound XI. Reaction of (Fe(H$_2$O)$_6$(NO$_3$)$_3$) with compound 23 in acetonitrile solvent at room temperature gave embodiment compound XII.

The reactions of Fe(II)-containing precursors with compounds 23 to 42 each formed dark blue-colored solutions immediately. Complexation of these ligands to the Fe(II) stabilizes the Fe in the +2 oxidation state.

Reactions of Fe(III)-containing precursors such as Fe(NO$_3$)$_3$.9H$_2$O with energetic ligands may also be used to obtain embodiment Fe(II) coordination complexes. The reaction mixtures in these cases are initially brown but change color from brown to blue after about 3 days. Attempts at isolating and characterizing the brown material were unsuccessful. The brown color is believed to be due to an initial formation of Fe(III) complexes that are subsequently reduced to Fe(II) by water, perhaps water coordinated to Fe(III) from precursor Fe(III) complex Fe(NO$_3$)$_3$·9H$_2$O.

The reaction rate and product yield may both be improved by adding an additional reducing agent to the reaction mixture. Addition of a stoichiometric amount of magnesium, for example, to the reaction mixture of Fe(NO$_3$)$_3$·9H$_2$O and compound 23 decreased the reaction time from about 3 days to about 30 minutes while improving the yield of compound II from 31% to 71%. A similar addition decreased the reaction time and improved the yield of compound XII from 28% to 62%. These observations are consistent with a mechanism involving initial coordination of energetic ligand to the Fe(III) center (the brown intermediate) followed by reduction of Fe(III) to Fe(II).

Embodiment coordination compounds I, II, XII, and XII are diamagnetic. These coordination complexes were analyzed by $^1$H NMR spectroscopy. The peaks in the $^1$H NMR spectra for the hydrogen atoms of the ligands were shifted downfield upon coordination to the metal center.

Figure 4:
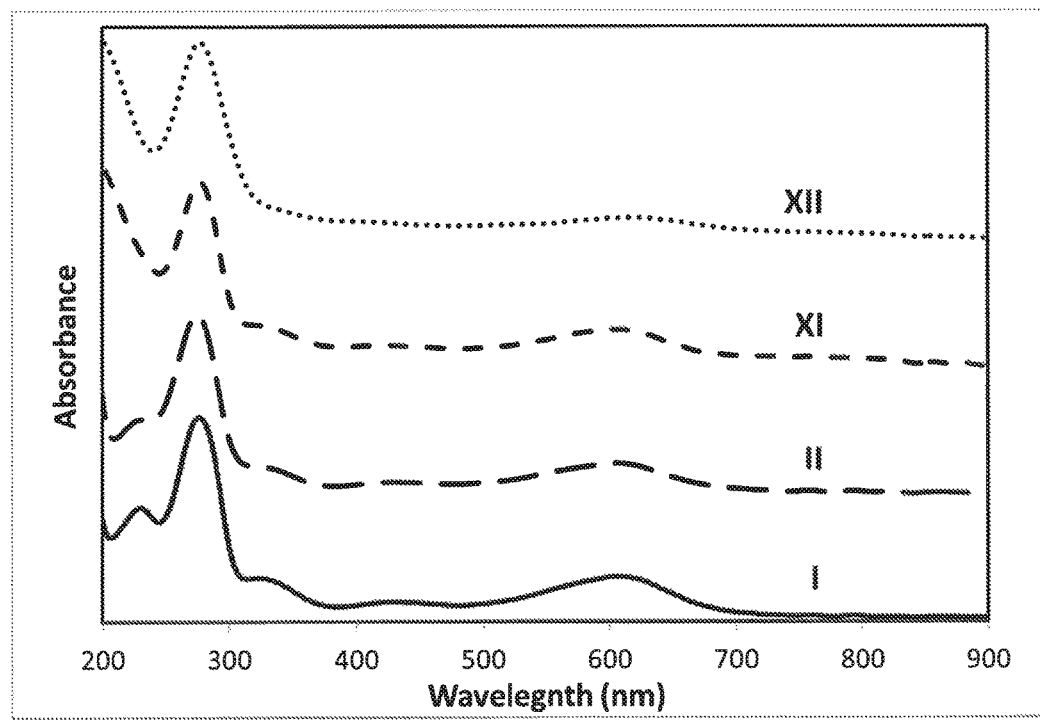
FIG. 4 shows UV-VIS spectra of I (solid black line), II (dashed line), XI (dashed line), and XII (dotted line) in MeCN solution.

FIG. 4 shows UV-vis spectra of coordination compounds I, II, XII, and XII. These UV-vis spectra include strong ligand-based absorbances near 270 nm, 330 nm, and 420 nm, in addition to a broad metal to ligand charge transfer band near 610 nm. No d-d transitions could be resolved for complexes I, II, XII, or XII.

Figure 5:
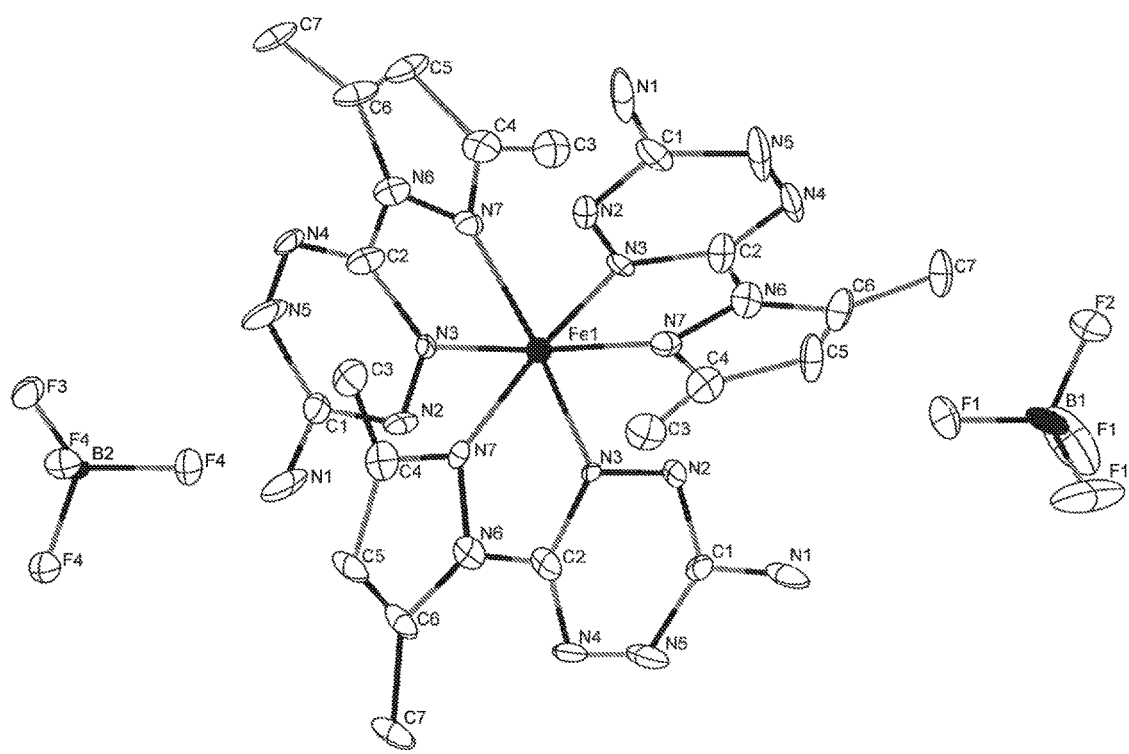
FIG. 5 shows a solid state structure of [(NH$_2$TzDMP)$_3$Fe][BF$_4$]$_2$ (compound I). H atoms and solvent omitted for clarity. Ellipsoids are at 40%.

FIG. 5 shows a solid state structure of [(NH$_2$TzDMP)$_3$Fe][BF$_4$]$_2$ (compound I). H atoms and solvent omitted for clarity. Ellipsoids are at 40%.

The octahedral complex of coordination compounds I, II, XII, and XII contains three ligands in a mer arrangement. The bite angle of each ligand is less than 90°. The metal-tetrazine distances for the complexes are 1.857(8) Å, 1.903(4) Å, 1.903(3) Å, and 1.900(2) Å respectively. These distances are shorter than those found in other structurally characterized iron-tetrazine complexes. The bond lengths and bond angles in the coordinated ligands are not significantly different from those in the corresponding uncoordinated ligands. While the bond lengths and angles in complexes of ligand 23 are largely consistent with complexes of ligand 31, the C—N bond distance between the NH$_2$ group and the tetrazine ring is approximately 0.03 Å shorter than the C—N bond distance between the DNAZ group and the tetrazine ring.

The embodiment coordination compound having the formula [(TriTzPyr)$_3$Fe][ClO$_4$]$_2$ was prepared by the reaction of hexaaquoiron(II)perchlorate (Fe(H$_2$O)$_6$(ClO$_4$)$_2$) with compound 44 in acetonitrile at room temperature. Scheme 4 below summarizes the reactions of Fe precursors with compounds 43 to 54.

Scheme 4

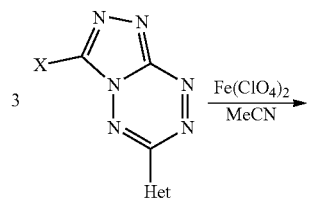

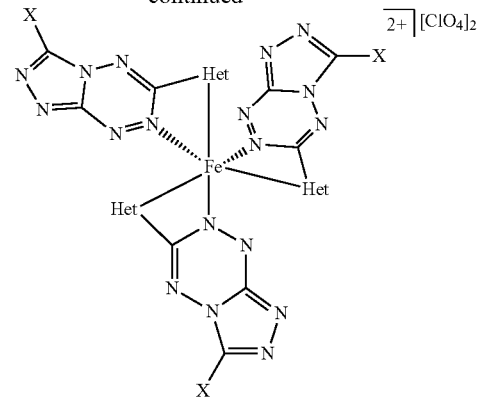

| | X = H | X = NH$_2$ | X = SH |
|---|---|---|---|
| Het = (pyrazole-CH$_3$, CH$_3$) | XXV | XXIX | XXXIII |
| Het = (pyrazole) | XXVI | XXX | XXXIV |
| Het = (pyrazole-NO2) | XXVII | XXXI | XXXV |
| Het = (triazole) | XXVIII | XXXII | XXXVI |

The reaction of hexaaquoiron(II)perchlorate (Fe(H$_2$O)$_6$(ClO$_4$)$_2$) with compound 44 in acetonitrile solvent at room temperature rapidly produced a blue colored solution from which embodiment coordination compound XXVI [(TriTz-Pyr)$_3$Fe][ClO$_4$]$_2$ was isolated in 77% yield. Reaction of (Fe(H$_2$O)$_6$(ClO$_4$)$_2$) with compound 48 in acetonitrile solvent at room temperature gave embodiment compound XXX in 80% yield.

Figure 6:
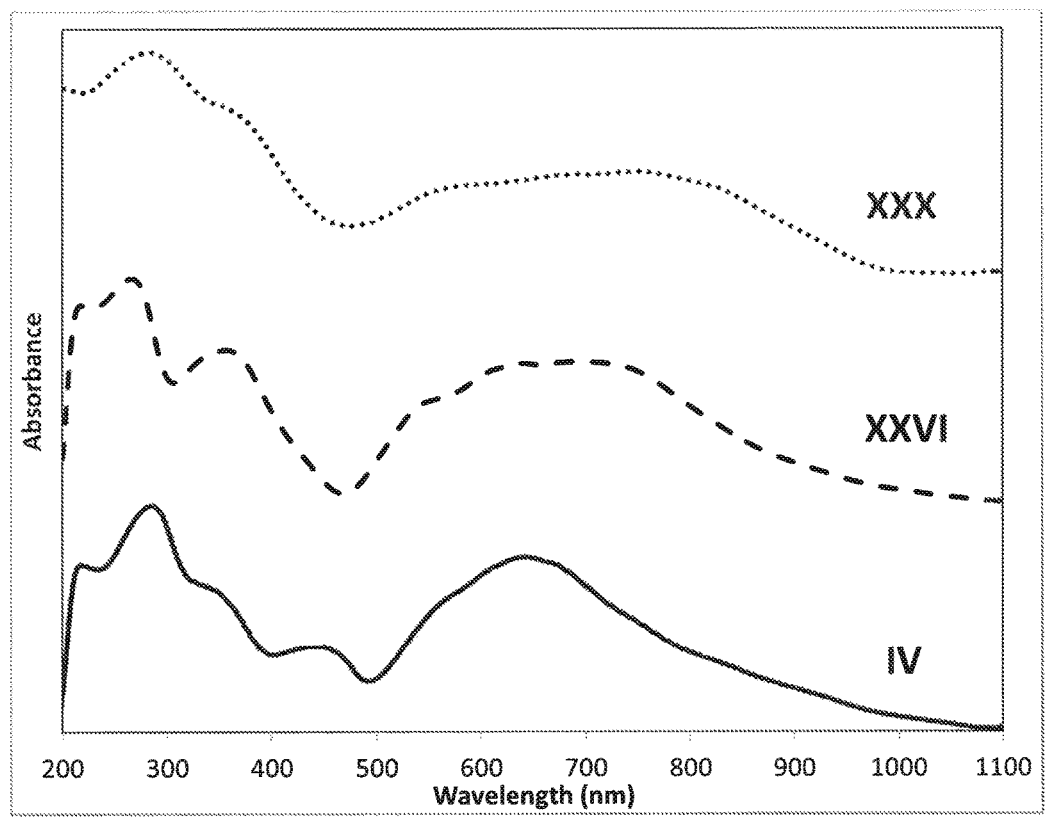
FIG. 6 shows UV-vis spectra of d-d transitions from 600 nm to 1100 nm of IV (solid black line), XXVI (dashed line), and XXX (dotted line) in MeCN solution.

The UV-vis spectra of coordination compounds IV, XXVI, XXX are given in FIG. 6. These spectra demonstrate the shift of the MLCT band to lower energies upon expansion of the ligand π system and the substitution of electron donating and withdrawing groups on the ligand backbone.

Embodiments also include coordination compounds of Cu with energetic ligands. Reaction of compound 23 or compound 31 with copper(II) precursor Cu(NO$_3$)$_2$·5/2H$_2$O afforded coordination compounds [(DMPTzNH$_2$)$_2$Cu(NO$_3$)][NO$_3$] (XXXVII) and [(DMPTzDNAZ)$_2$Cu(NO$_3$)][NO$_3$] (XLI) in 91% and 79% isolated yield respectively. The copper(II) chemistry results in ligand to metal ratio of 2:1 rather than the 3:1 ratio observed for the Fe(II) chemistry. The difference in coordination number may be a consequence of Jahn-Teller distortion generally associated with d$^9$ metal centers and a limited flexibility of ligands 23 and 31. Reactions of copper precursors with compounds 23, 24, 27, 28, 31, 32, 35, 36, 39, and 40 are summarized in Scheme 5 below.

Scheme 5

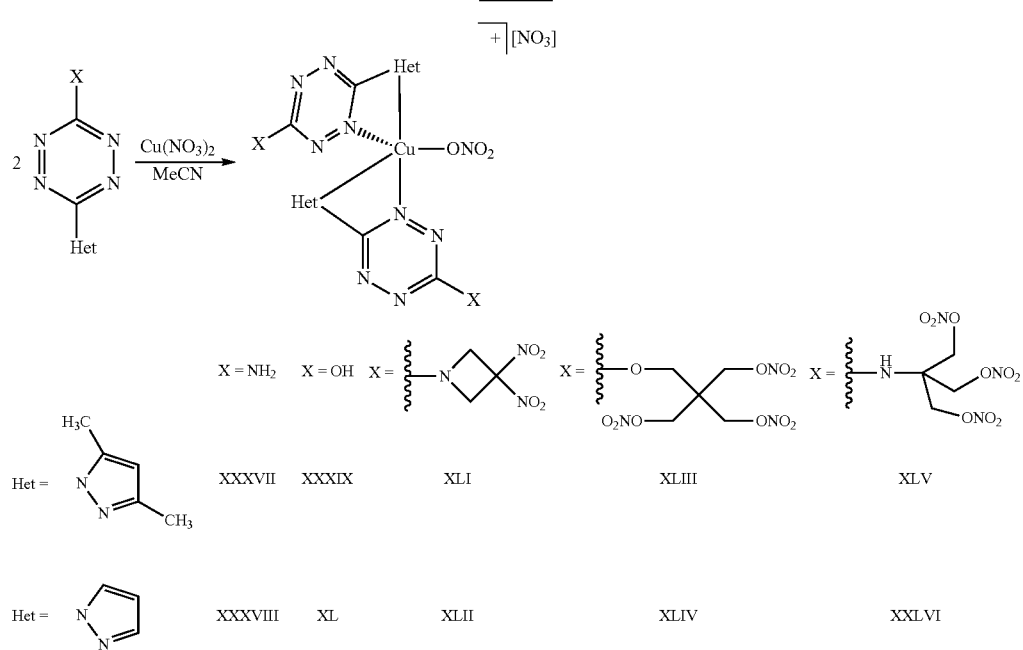

Figure 7:
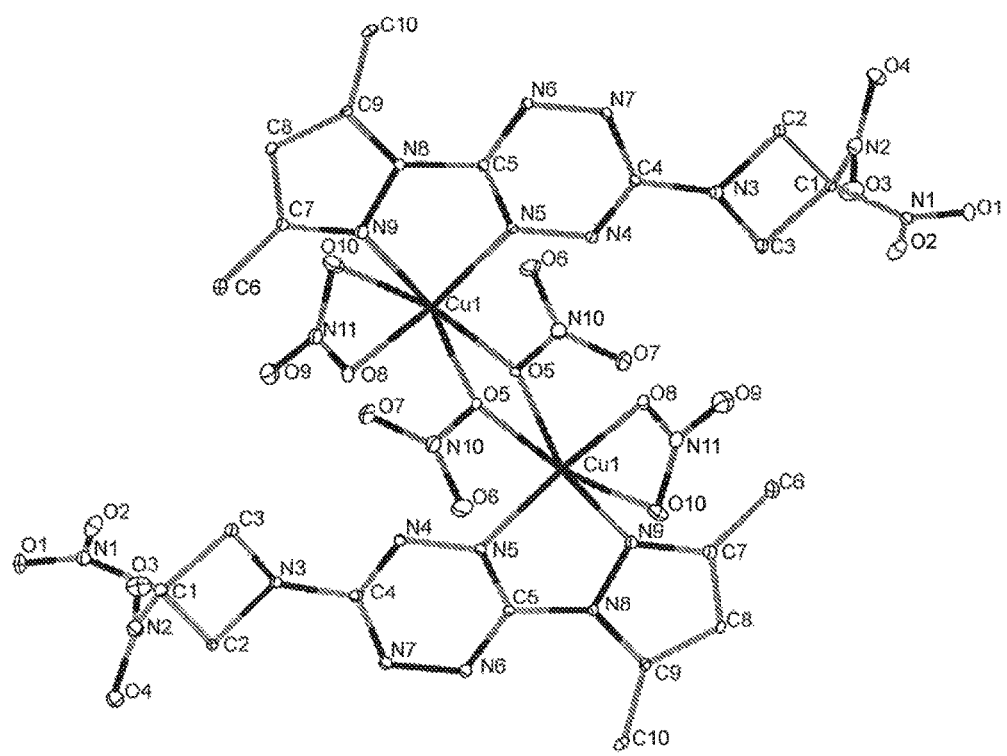
FIG. 7 shows a solid state structure of an embodiment compound.

FIG. 7 shows a solid state structure of [(DMPTzDNAZ)Cu(NO₃)₂]₂ (compound XLI). H atoms and solvent omitted for clarity. Ellipsoids are at 40%.

Embodiments also include coordination compounds of Cu with energetic ligands in a 1:1 ratio. Reaction of compound 23 or compound 31 with copper(II) precursor Cu(NO₃)₂·5/2H₂O afforded coordination compounds [(DMPTzNH₂)Cu(NO₃)₂]₂ (XLVII) and [(DMPTzDNAZ)Cu(NO₃)₂]₂ (XLVIII) in 77% isolated yield each. The compounds form dimeric structures with two ligands and two copper centers. The nitrate ligands adopt two different coordination geometries, either terminal or bridging. A summary of the reactions of copper precursors with compounds 23, 27, 31, 35, and 39 in a 1:1 ratio are summarized in scheme 6 below.

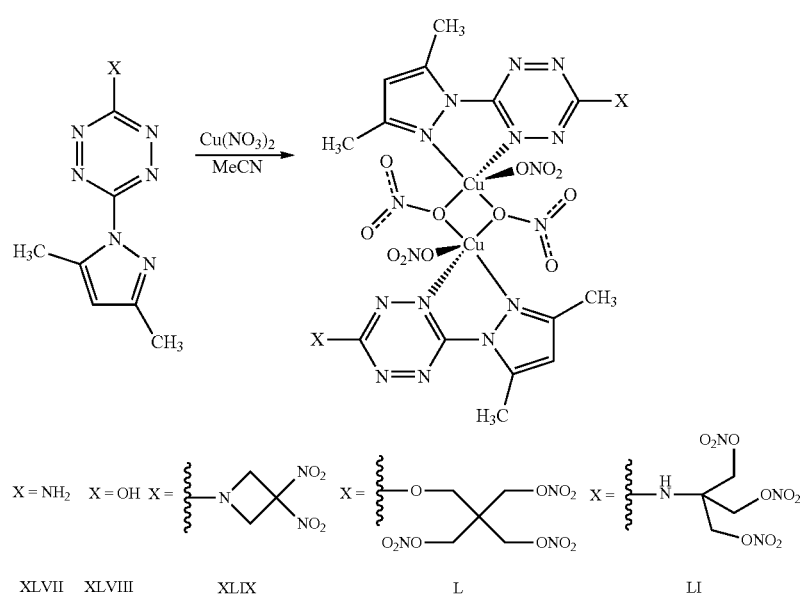

Embodiments also include coordination compounds of Cu(I) metal centers with energetic ligands in a 1:2 ratio. Reaction of the copper(I) precursor Cu(CH₃CN)₄(PF₆) with compound 23 afforded [(DMPTzNH₂)₂Cu][PF₆] (LII) in 91% yield. Reaction of the copper(I) precursor Cu(CH₃CN)₄(PF₆) with compound 31 afforded [(DMPTzDN-AZ)₂Cu][PF₆] (LIII) in 88% yield. Compounds LII and LIII each include a cationic, diamagnetic, tetrahedral complex. A summary of the reactions of Cu(CH₃CN)₄(PF₆) with 23 and 31 are outlined below in scheme 7.

coordinate Cu complexes. The solid state structure of compound LIII, which is shown in FIG. 10, includes a Cu(I) center, two ligands that coordinate to the Cu center, and a nitrate counterion. Compounds LII and LIII are best described as distorted tetrahedral complexes with $\tau_4$ values of 0.750 and 0.574 respectively.

Embodiment compounds also include first row transition metals Co and Ni. Reaction of hexa-aquocobalt(II)nitrate (Ni(NO₃)₂·6H₂O) with compound 23 afforded [(DMPTzNH₂)₃Ni][NO₃]₂ (LIV), as shown in Scheme 8 below.

Scheme 7

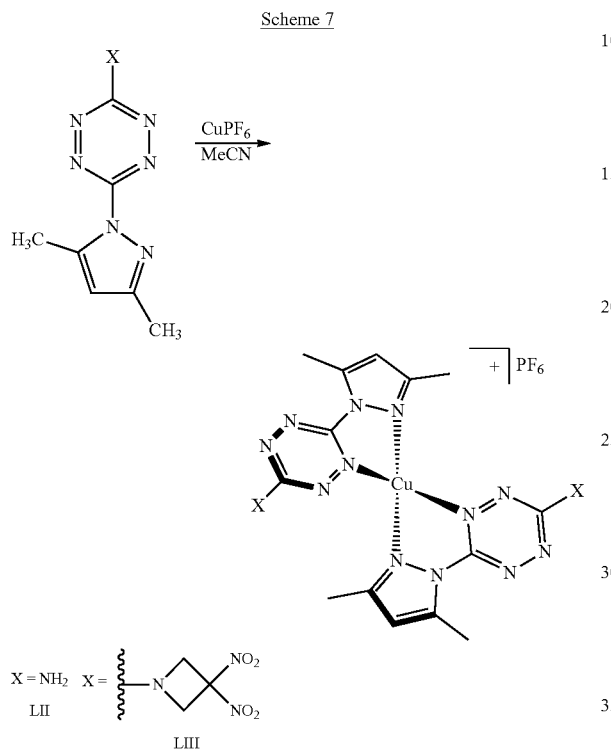

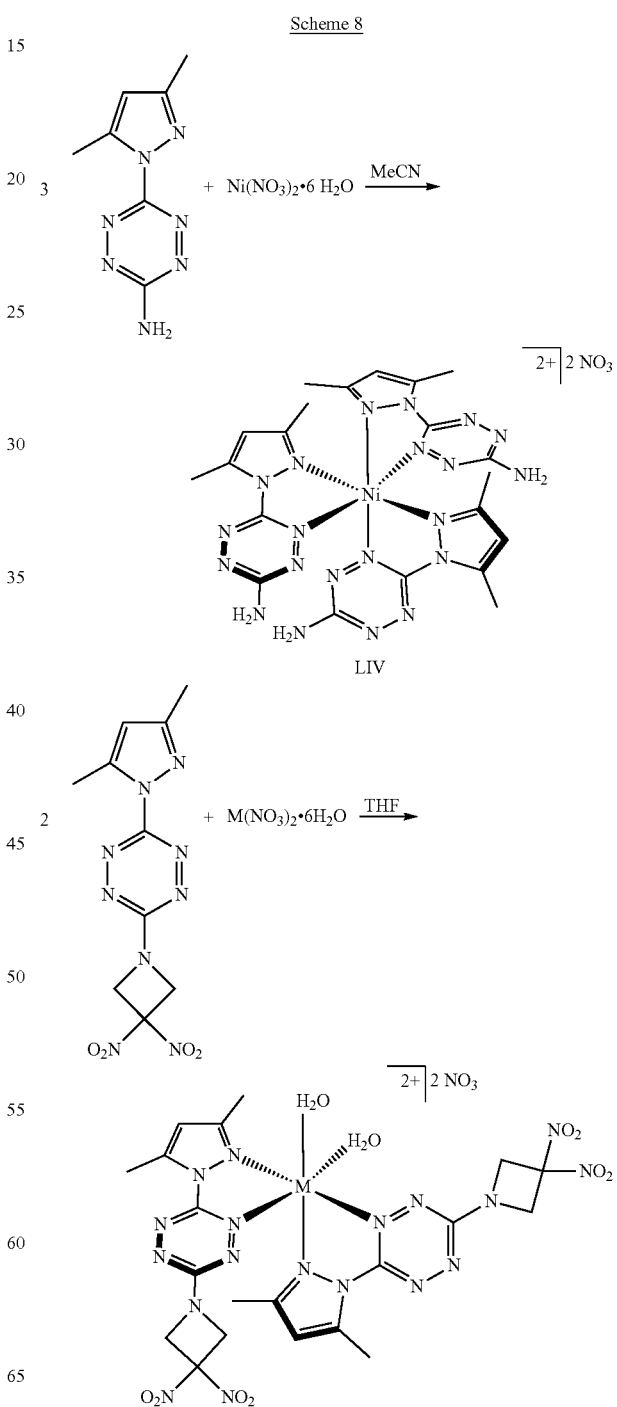

Compounds LII and LIII each include a cationic, diamagnetic, tetrahedral complex. Compounds LII and LIII were purple in the solid state but orange-brown in a solution of acetonitrile. Ligand coordination to Cu(I) does not result in any significant change in the ¹H NMR spectra for hydrogen atoms on the ligand.

Figure 8:
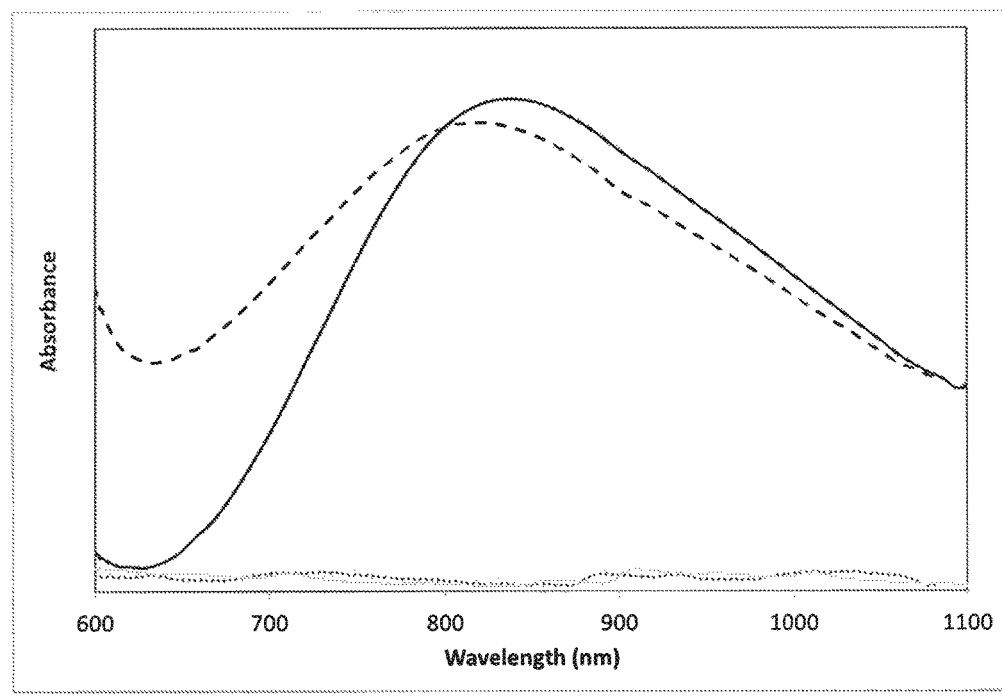
FIG. 8 shows a UV-vis spectra for several compounds.
Figure 9:
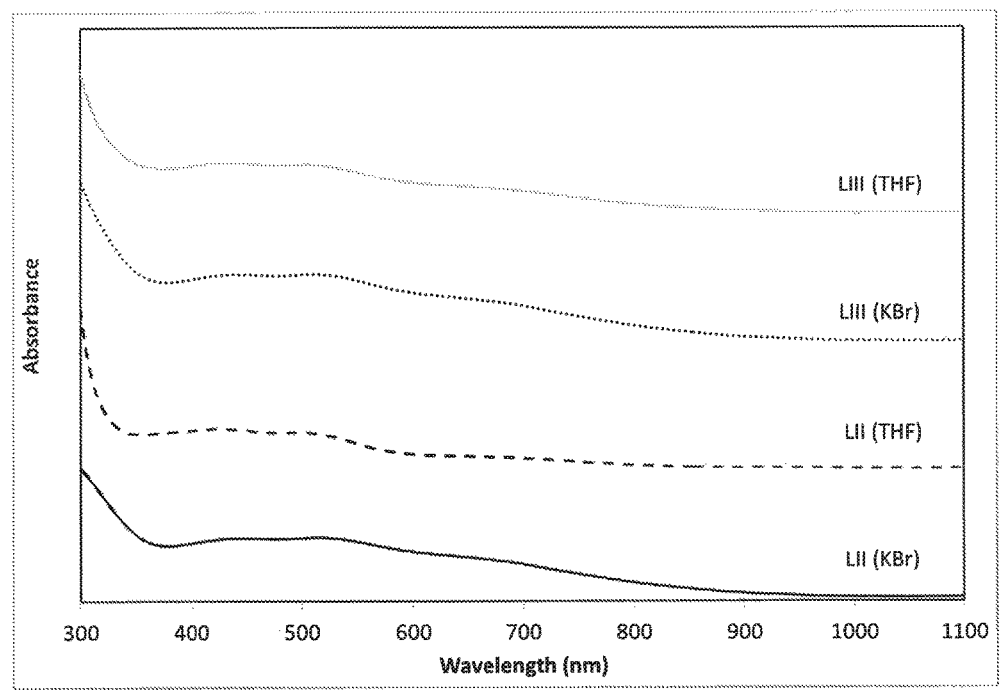
FIG. 9 compares solid state UV-vis spectra with solution UV-vis spectra for compounds LII and LIII.

FIG. 8 shows UV-vis spectra of d-d transitions from 600 nm to 1100 nm of XXXVII (solid black line), XLI (dashed line), LII (dotted line), and LIII (solid grey line) in MeCN solution. The spectra do not include metal to ligand charge transfer bands ("MLCT bands"). This was unexpected for Cu(I)-containing complexes LII and LIII because such MLCT bands were reported in the UV-vis spectra for known Cu(I) complexes with other tetrazine ligands. This prompted us to obtain UV-vis spectra for these compounds in the solid state (FIG. 9). Unlike the solution-based spectra, the solid state spectra include a broad MLCT band at 690 nm. MLCT bands were also observed for solutions of LII and LIII in a different solvent (THF).

A slight shift in the frequency and an increased intensity of the ligand-based π to π* and n to π* transitions was observed in the UV-vis spectra of LII and LIII.

Broad absorptions at 820 (compound XXXVII) and 810 nm (compound XLI) were assigned as d-d transitions, which are typical of five-coordinate Cu(II) complexes.

Thus, compounds XXXVII and XLI are five coordinate Cu complexes with geometries of that are best described as distorted square pyramidal with $\tau_5$ values of 0.211 and 0.222 respectively. By contrast, compounds LII and LIII are four -continued M = Ni  LV
M = Co  LVII

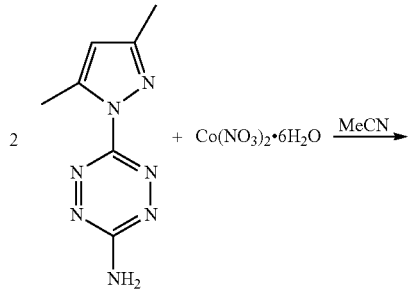

LVI

Reaction of (Ni(NO$_3$)$_2$·6H$_2$O) with compound 31 afforded ([(DMPTzDNAZ)$_2$Ni(H$_2$O)$_2$][NO$_3$]$_2$) (compound LV).

Reaction of (Co(NO$_3$)$_2$·6H$_2$O) with compound 23 afforded ([(DMPTzNH$_2$)$_2$Co(H$_2$O)(NO$_3$)][NO$_3$]) (compound LVI). Compound LVI includes an octahedral cationic complex and bound nitrate counterion.

Reaction of (Co(NO$_3$)$_2$ 6H$_2$O) with compound 31 afforded ([(DMPTzDNAZ)$_2$Co(H$_2$O)$_2$][NO$_3$]$_2$) (compound LVII).

Compounds LV, LVI and LVII each contain an octahedral complex with two tetrazine ligands coordinated to the metal center. Apparently, the lower steric demand of ligand 23 permits the nitrate counterion to coordinate to the Co center, but a larger steric demand of ligand 31 does not, and is likely responsible for replacement of nitrate by water in the coordination sphere of the Co center. Apparently, a low steric demand of ligand 23 permitted three of these ligands to coordinate to the Ni(II) center in LV.

X-ray structures for compounds LIV, LV, LVI, and LVII confirm the formulas shown in Schemes 5 and 6. The X-ray structures for LV, LVI, and LVII reveal a distorted octahedral geometry for the cationic portion with only two energetic ligands bound to the metal center. The X-ray structure for compound LIV reveals a distorted octahedral geometry for the cationic portion with three ligands bound to the nickel center.

The electrochemical properties of the complexes were investigated by cyclic voltammetry ("CV") experiments performed in 0.1M NBu$_4$PF$_6$ acetonitrile solutions.

The iron complexes I, II, XI, and XII showed similar behavior to one another. Each showed three distinct reduction events from −0.40V to −1.18V, which likely correspond to the reduction of each of the tetrazine ligands to the radical anion. The tetrazine reductions in the complexes were shifted more positive relative to those of the uncoordinated ligands 23 and 31, likely due to a stabilization provided by the divalent metal center. Similar behavior for iron complexes of 3,6-bis(2-pyridyl)-1,2,4,5-tetrazine) has been reported. In addition to the reductions, each of the four iron complexes shows an oxidation event between 1.18V and 1.33V that corresponds to a Fe$^{II}$/Fe$^{III}$ couple. The highly anodic potential of the Fe$^{II}$/Fe$^{III}$ couple is consistent with prior observations that ligands with higher nitrogen character have more anodic Fe$^{II}$/Fe$^{III}$ couples. The extreme potential of the Fe$^{II}$/Fe$^{III}$ couple also support our assignment of water as the reducing agent in the absence of an external reductant.

The copper complexes XXXVII, XLI, LII, and LIII showed similar electrochemical behavior to one another. Each displays a redox couple ranging from 0.25 V to 0.41 V corresponding to the Cu$^I$/Cu$^{II}$ couple. The anodic shift of the Cu$^I$/Cu$^{II}$ couple may be explained by a high nitrogen electron deficient tetrazine ligand leading to an air stable copper (I) complex. Each copper complex also shows a single irreversible reduction event between −0.62V and −0.72V. This reduction could be attributable to a reduction of one of the tetrazine ligands to the radical anion, or to a Cu$^I$/Cu$^0$ couple. The reduction is likely ligand based because no stable complex of Cu$^0$ has yet been isolated. The MLCT band in UV-vis spectra for LII and for LIII is likely due to a tetrazine reduction because the MLCT transition involves a formal oxidation of the metal and reduction of the ligand. Similar behavior has been reported for copper complexes of bis(tetrazine)pyridine.

The redox behavior of cobalt complexes LVI and LVII and of the nickel complexes LIV and LV was more difficult to assign.

Overall, the redox behavior of the complexes included a variety of reversible metal and ligand based reductions at potentials that were relatively unaffected by substitution of explosive for inert groups.

Synthesis of [(DMPTzNH$_2$)$_3$Fe][BF$_4$]$_2$ (I). A solution of compound 23 ("DMPTzNH$_2$", 0.191 g, 1.00 mmol) and Fe(BF$_4$)$_2$·6H$_2$O (0.133 g, 0.334 mmol) in acetonitrile ("MeCN") solvent (5 mL) was prepared. Compound 23 has the structure

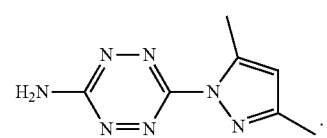

23

The solution turned dark blue seconds after the ingredients were combined. The dark blue solution was stirred for 30 minutes, after which solvent was removed in vacuo until approximately 2 mL of acetonitrile remained, and then diethyl ether (2 mL) was added to precipitate the product [(DMPTzNH$_2$)$_3$Fe][BF$_4$]$_2$ (I, 0.220 g, 82%), isolated as a dark blue powder. Single crystals suitable for X-ray diffraction were grown by cooling a concentrated MeCN solution at 0° C. for two days. $^1$HNMR (400 MHz, d$_3$-MeCN) δ 6.74 (s, 2H, NH$_2$), 6.49 (s, 1H, Pyr-H), 2.82 (s, 3H, CH$_3$), 1.79 (s, 3H, CH$_3$). UV-Vis spectrum (MeCN) λ$_{max}$ (ε$_M$): 276 (82,630), 334 (15,940), 434 (6,500), 611 (br, 16,670) nm (L mol$^{-1}$ cm$^{-1}$). Elemental analysis calculated for C$_{21}$H$_{27}$B$_2$F$_8$FeN$_{21}$: C, 31.41%, H, 3.39%, N, 36.63%. Found: C, 31.08%, H, 3.70%, N, 35.10%.

Synthesis of [(DMPTzNH$_2$)$_3$Fe][NO$_3$]$_2$ (II). (Method A) A solution of compound 23 ("DMPTzNH$_2$", 0.191 g, 1.00 mmol) in MeCN (5 mL) was prepared. Fe(NO₃)₃·9H₂O (0.134 g, 0.333 mmol) was added to form a dark yellow solution. The initial dark yellow solution was stirred for 3 days until it was a uniform deep blue color. The solvent was reduced in vacuo until 2 mL of MeCN remained, then diethyl ether (2 mL) was added and the solution cooled to 0° C. overnight. A dark blue precipitate was collected via filtration and recrystallized from a concentrated MeCN solution. The product, [(DMPTzNH₂)₃Fe][NO₃]₂(II, 0.084 g, 31%) was collected as dark blue crystals suitable for single crystal diffraction. ¹HNMR (400 mHz, d₆-acetone) δ 7.00 (s, 2H, NH₂), 6.59 (s, 1H, Pyr-H), 2.92 (s, 3H, CH₃), 1.89 (s, 3H, CH₃). UV-Vis spectrum (MeCN) $\lambda_{max}$ ($\varepsilon_M$): 272 (79,120), 333 (15,470), 432 (7,960), 609 (br, 13,810) nm (L mol⁻¹ cm⁻¹).

Synthesis of [(NH₂TzDMP)₃Fe][ClO₄]₂ (III). A solution of 23 ("DMPTzNH₂", 1.92 g, 10.0 mmol) in MeCN (5 mL) was added to a stirred solution of [Fe(H₂O)₆][ClO]₂ (1.21 g, 3.33 mmol) in MeCN (10 mL). The solution as stirred for 15 minutes until it was a uniform blue color. Diethyl ether (10 mL) was added, and [(NH₂TzDMP)₃Fe][ClO₄]₂ (III, 2.10 g, 78%) was collected as a dark blue solid via filtration. Single crystals of III were grown from a concentrated MeCN solution at 0° C. over 3 days. UV-Vis spectrum (KBr pellet) 288 (1.00), 351 (0.70), 459 (0.57), 651 (0.94) $\lambda_{max}$ (relative intensity). Anal. Calcd for C₂₁H₂₇Cl₂FeN₂₁O₈: C, 30.45%, H, 3.29%, N, 35.51%. Found: C, 30.60%, H, 3.16, N, 34.42.

Synthesis of [(NH₂TzPyr)₃Fe][ClO₄]₂ (IV). A suspension of 24 ("PyrTzNH₂", 1.63 g, 10.0 mmol) in MeCN (5 mL) was added to a stirred solution of [Fe(H₂O)₆][ClO₄]₂ (1.21 g, 3.33 mmol) in MeCN (5 mL). Compound 24 has the structure

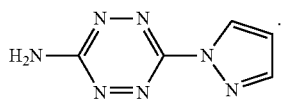

24

The solution as stirred for 15 minutes until it was a uniform violet color. Diethyl ether (10 mL) was added, and [(NH₂TzPyr)₃Fe][ClO₄]₂ (IV, 2.06 g, 83%) was collected as a dark blue solid via filtration. Single crystals of IV were grown from the diffusion of diethyl ether into a concentrated MeCN solution over 2 days. δ. UV-Vis spectrum (KBr pellet) 284 (1.00), 345 (0.63), 448 (0.38), 560 (0.59), 639 (0.77) $\lambda_{max}$ (relative intensity). Anal. Calcd for C₁₅H₁₅Cl₂FeN₂₁O₈·C₂H₃N: C, 26.00%, H, 2.31%, N, 39.24%. Found: C, 25.99%, H, 2.29%, N, 39.38%.

Synthesis of [(NH₂Tz(NO₂Pyr))₃Fe][ClO₄]₂ (V). A suspension of 25 ("(NO₂Pyr)TzNH₂", 0.208 g, 1.0 mmol) in MeCN (2 mL) was added to a stirred solution of [Fe(H₂O)₆][ClO₄]₂ (0.121 g, 0.333 mmol) in MeCN (2 mL). Compound 25 has the structure

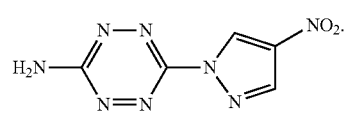

25

The solution was stirred for 2 hours at room temperature until the solution was a uniform red-purple color. Diethyl ether (10 mL) was added to precipitate [(NH₂Tz(NO₂Pyr))₃Fe][ClO₄]₂ (V, 0.242 g, 82.7%) as a purple solid.

Synthesis of [(NH₂TzTrz)₃Fe][ClO₄]₂ (VI). A suspension of 26 ("TrzTzNH₂", 1.64 g, 10.0 mmol) in acetone (5 mL) was added to a stirred solution of [Fe(H₂O)₆][ClO₄]₂ (1.21 g, 3.33 mmol) in acetone (5 mL). Compound 26 has the structure

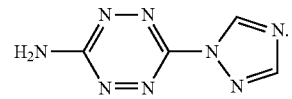

26

The solution was stirred for 4 hours at 50° C. until the solution was a uniform purple color. Hexane (20 mL) was added to precipitate [(NH₂TzTrz)₃Fe][ClO₄]₂ (VI, 1.670 g, 67.1%) as a lime green solid. The complex is solvo-chromatic returning to a purple color in solution.

Synthesis of [(HOTzDMP)₃Fe][ClO₄]₂ (VII). A suspension of 27 ("DMPTzOH", 1.92 g, 10.0 mmol) in MeCN (5 mL) was added to a stirred solution of [Fe(H₂O)₆][ClO₄]₂ (1.21 g, 3.33 mmol) in MeCN (5 mL). Compound 27 has the structure

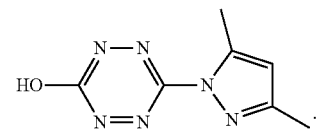

27

The solution was stirred for 1 hour at room temperature until the solution was a uniform blue color. Diethyl ether (20 mL) was added to precipitate [(HOTzDMP)₃Fe][ClO₄]₂ (VII, 1.85 g, 66.9%) as an intensely blue solid.

Synthesis of [(HOTzPyr)₃Fe][ClO₄]₂ (VIII). A suspension of 28 ("PyrTzOH", 1.64 g, 10.0 mmol) in MeCN (5 mL) was added to a stirred solution of [Fe(H₂O)₆][ClO₄]₂ (1.21 g, 3.33 mmol) in MeCN (5 mL). Compound 28 has the structure

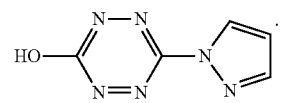

28

The solution was stirred for 1 hour at room temperature until the solution was a uniform blue color. Diethyl ether (20 mL) was added to precipitate [(HOTzPyr)₃Fe][ClO₄]₂ (VIII, 1.46 g, 58.7%) as an intensely blue solid.

Synthesis of [(HOTz(NO₂Pyr))₃Fe][ClO₄]₂ (IX). Complex IX can be synthesized in an analogous method by combining a suspension of 29 ("(NO₂Pyr)TzOH", 0.209 g, 1.00 mmol) in MeCN (2 mL) and a solution of [Fe(H₂O)₆][ClO₄]₂ (0.121 g, 0.333 mmol) in MeCN (5 mL). Compound 29 has the structure

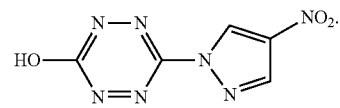

29

Diethyl ether can be added to precipitate product which can be collected via filtration.

Synthesis of [(HOTzTrz)₃Fe][ClO₄]₂ (X). Complex X can be synthesized in an analogous method by combining a suspension of 30 ("TrzTzOH", 0.165 g, 1.00 mmol) in MeCN (2 mL) and a solution of [Fe(H₂O)₆][ClO₄]₂ (0.121 g, 0.333 mmol) in MeCN (5 mL). Compound 30 has the structure

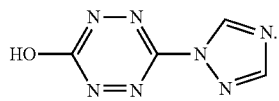

Diethyl ether can be added to precipitate product which can be collected via filtration.

Synthesis of [(DMPTzDNAZ)₃Fe][BF₄]₂ (XI). A solution of compound 31 ("DMPTzDNAZ", 0.321 g, 1.00 mmol) in THF (5 mL) was prepared. Compound 31 has the structure

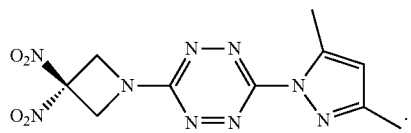

Fe(BF₄)₂.6H₂O (0.133 g, 0.334 mmol) was added, and a few seconds later, the solution became dark blue. The dark blue solution was stirred for 30 minutes. Hexane (5 mL) was added to precipitate the product [(DMPTzNH₂)₃Fe][BF₄]₂ (XI, 0.254 g, 76%), which was isolated as a dark blue powder. Single crystals suitable for X-ray diffraction were grown by cooling a concentrated MeCN solution at 0° C. for two days. ¹HNMR (400 MHz, d₆-acetone) δ 6.70 (s, 1H, pyrazole), 5.13 (s, 4H, DNAZ), 2.91 (s, 6H, CH₃). UV-Vis spectrum (MeCN) $\lambda_{max}$ ($\varepsilon_M$): 277 (80,420), 331 (13,520), 427 (6,240), 607 (br, 14,510) nm (L mol⁻¹ cm⁻¹).

Synthesis of [(DMPTzDNAZ)₃Fe][NO₃]₂ (XII). A solution of compound 31 ("DMPTzDNAZ", 0.321 g, 1.00 mmol) in MeCN (5 mL) was prepared. Fe(NO₃)₃.9H₂O (0.134 g, 0.333 mmol) and magnesium (0.004 g, 0.167 mmol) were added and the mixture was stirred. Within 5 minutes, the mixture turned to a dark blue color. Stirring continued at room temperature for an additional 2 hours. The solution was concentrated to a volume of approximately 1 mL of MeCN under vacuum and then diethyl ether (3 mL) was added to precipitate the product [(DMPTzDNAZ)₃Fe][NO₃]₂ (XII, 0.196 g, 62%) as a dark blue powder. Crystals suitable for single crystal X-ray diffraction were grown from the slow diffusion of diethyl ether into a concentrated MeCN solution at 0° C. overnight. ¹HNMR (400 MHz, d₆-acetone) δ 6.21 (s, 1H, pyrazole), 5.46 (s, 4H, Dnaz), 2.93 (s, 6H, CH₃). UV-Vis spectrum (MeCN) $\lambda_{max}$ ($\varepsilon_M$): 276 (78050), 334 (14,770), 415 (6,660), 620 (13,310) nm (L mol⁻¹ cm⁻¹).

Synthesis of [(DNAZTzDMP)₃Fe][ClO₄]₂ (XIII). Complex XIII can be synthesized in an analogous method by combining a suspension of 31 ("DMPTzDNAZ", 0.321 g, 1.00 mmol) in MeCN (2 mL) and a solution of [Fe(H₂O)₆][ClO₄]₂ (0.121 g, 0.333 mmol) in MeCN (5 mL). Diethyl ether can be added to precipitate product which can be collected via filtration.

Synthesis of [(DNAZTzPyr)₃Fe][ClO₄]₂ (XIV). Complex XIV can be synthesized in an analogous method by combining a suspension of 32 ("DNAZTzPyr", 0.293 g, 1.00 mmol) in MeCN (2 mL) and a solution of [Fe(H₂O)₆][ClO₄]₂ (0.121 g, 0.333 mmol) in MeCN (5 mL). Compound 32 has the structure

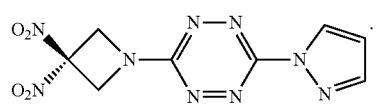

Diethyl ether can be added to precipitate product which can be collected via filtration.

Synthesis of [(DNAZTz(N₂Pyr))₃Fe][ClO₄]₂ (XV). Complex XV can be synthesized in an analogous method by combining a suspension of 33 ("DNAZTz(NO₂Pyr)", 0.338 g, 1.00 mmol) in MeCN (2 mL) and a solution of [Fe(H₂O)₆][ClO₄]₂ (0.121 g, 0.333 mmol) in MeCN (5 mL). Compound 33 has the structure

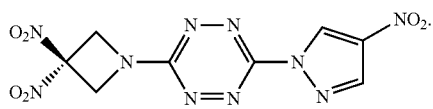

Diethyl ether can be added to precipitate product which can be collected via filtration.

Synthesis of [(DNAZTzTrz)₃Fe][ClO₄]₂ (XVI). Complex XVI can be synthesized in an analogous method by combining a suspension of 34 ("DNAZTzTrz", 0.294 g, 1.00 mmol) in MeCN (2 mL) and a solution of [Fe(H₂O)₆][ClO₄]₂ (0.121 g, 0.333 mmol) in MeCN (5 mL). Compound 32 has the structure

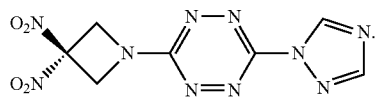

Diethyl ether can be added to precipitate product which can be collected via filtration.

Synthesis of [(PETriNTzDMP)₃Fe][ClO₄]₂ (XVII). A suspension of 35 ("PETriNTzDMP", 0.445 g, 1.0 mmol) in THF (2 mL) was added to a stirred solution of [Fe(H₂O)₆][ClO₄]₂ (0.121 g, 0.333 mmol) in THF (2 mL). Compound 35 has the structure

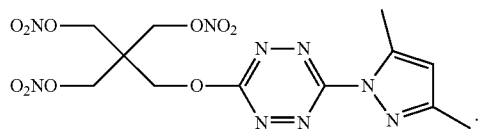

The solution was stirred for 1 hour at room temperature until the solution was a uniform blue color. Hexane (10 mL) was added to precipitate [(PETriNTzDMP)₃Fe][ClO₄]₂ (XVII, 0.339 g, 64.1%) as an intensely blue solid.

Synthesis of [(PETriNTzPyr)₃Fe][ClO₄]₂ (XVIII). Complex XVIII can be synthesized in an analogous method by combining a suspension of 36 ("PETriNTzPyr", 0.417 g, 1.00 mmol) in MeCN (2 mL) and a solution of [Fe(H₂O)₆][ClO₄]₂ (0.121 g, 0.333 mmol) in MeCN (2 mL). Compound 36 has the structure

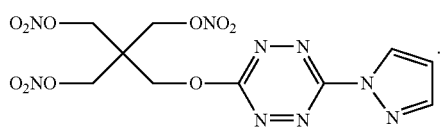

Diethyl ether can be added to precipitate product which can be collected via filtration.

Synthesis of [(PETriNTz(N₂Pyr) Fe][ClO₄]₂ (XIX). Complex XIX can be synthesized in an analogous method by combining a suspension of 37 ("PETriNTz(NO₂Pyr)", 0.462 g, 1.00 mmol) in MeCN (2 mL) and a solution of [Fe(H₂O)₆][ClO₄]₂ (0.121 g, 0.333 mmol) in MeCN (2 mL). Compound 37 has the structure

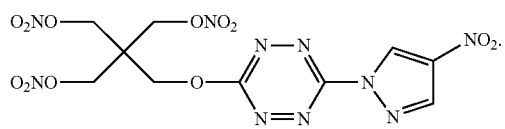

Diethyl ether can be added to precipitate product which can be collected via filtration.

Synthesis of [(PETriNTzTrz)₃Fe][ClO₄]₂ (XX). Complex XX can be synthesized in an analogous method by combining a suspension of 38 ("PETriNTzTrz", 0.418 g, 1.00 mmol) in MeCN (2 mL) and a solution of [Fe(H₂O)₆][ClO₄]₂ (0.121 g, 0.333 mmol) in MeCN (2 mL). Compound 38 has the structure

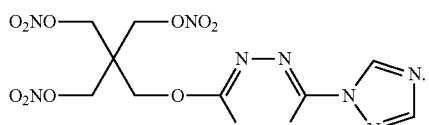

Diethyl ether can be added to precipitate product which can be collected via filtration.

Synthesis of [(TrisNTzDMP)₃Fe][ClO₄]₂ (XXI). A suspension of 39 ("TrisNTzDMP", 0.430 g, 1.0 mmol) in THF (2 mL) was added to a stirred solution of [Fe(H₂O)₆][ClO₄]₂ (0.121 g, 0.333 mmol) in THF (2 mL). Compound 39 has the structure

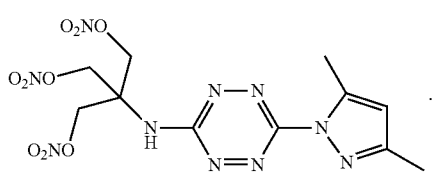

The solution was stirred for 1 hour at room temperature until the solution was a uniform blue color. Hexane (10 mL) was added to precipitate [(TrisNTzDMP)₃Fe][ClO₄]₂ (XXI, 0.361 g, 71.7%) as an dark blue solid.

Synthesis of [(TrisNTzPyr)Fe][ClO₄]₂ (XXII). A suspension of 40 ("TrisNTzPyr", 0.402 g, 1.0 mmol) in THF (2 mL) was added to a stirred solution of [Fe(H₂O)₆][ClO₄]₂ (0.121 g, 0.333 mmol) in THF (2 mL). Compound 40 has the structure

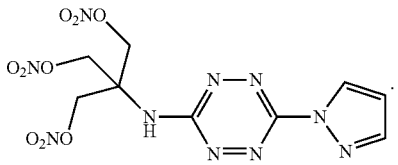

The solution was stirred for 1 hour at room temperature until the solution was a uniform blue color. Hexane (10 mL) was added to precipitate of [(TrisNTzPyr)₃Fe][ClO₄]₂ (XXII, 0.268 g, 55.0%) as an intensely blue-purple solid.

Synthesis of [(TrisNTz(NO₂Pyr))₃Fe][ClO₄]₂ (XXIII). Complex XXIII can be synthesized in an analogous method by combining a suspension of 41 ("TrisNTz(NO₂Pyr)", 0.447 g, 1.00 mmol) in MeCN (2 mL) and a solution of [Fe(H₂O)₆][ClO₄]₂ (0.121 g, 0.333 mmol) in MeCN (2 mL). Compound 41 has the structure

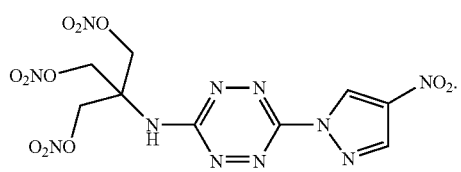

Diethyl ether can be added to precipitate product which can be collected via filtration.

Synthesis of [(TrisNTzTrz)₃Fe][ClO₄]₂ (XXIV). Complex XXIV can be synthesized in an analogous method by combining a suspension of 42 ("TrisNTzTrz", 0.447 g, 1.00 mmol) in MeCN (2 mL) and a solution of [Fe(H₂O)₆][ClO₄]₂ (0.121 g, 0.333 mmol) in MeCN (2 mL). Compound 42 has the structure

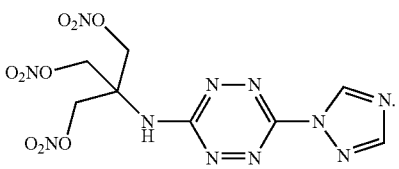

Diethyl ether can be added to precipitate product which can be collected via filtration.

Synthesis of [(TriTzDMP)₃Fe][ClO₄]₂ (XXV). A solution of 43 ("TriTzDMP", 2.16 g, 10.0 mmol) in MeCN (5 mL) was added to a stirred solution of [Fe(H₂O)₆][ClO₄]₂ (1.21 g, 3.33 mmol) in MeCN (5 mL). Compound 43 has the structure

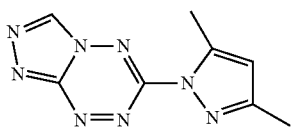

43

The solution as stirred for 15 minutes until it was a uniform blue color. Diethyl ether (10 mL) was added, and [(TriTzDMP)$_3$Fe][ClO$_4$]$_2$ (XXV, 2.43 g, 81%) was collected as a dark blue solid via filtration. $^1$HNMR (400 mHz, d$_6$-DMSO) 2.18 (s, 3H, CH$_3$), 2.51 (s, 3H, CH$_3$), 6.27 (s, 1H, pyr-CH), 9.94 (s, 1H, triazolo-CH) δ. UV-Vis spectrum (KBr pellet) 269 (1.00), 368 (0.55), 550 (0.30), 646 (0.50), 741 (0.53) λ$_{max}$ (relative intensity). Anal. Calcd for C$_{24}$H$_{24}$Cl$_2$FeN$_{24}$O$_8$·C$_2$H$_3$N: C, 33.06%, H, 2.88%, N, 37.08%. Found: C, 33.17%, H, 2.97%, N, 37.01%.

Synthesis of [(TriTzPyr)$_3$Fe][ClO$_4$]$_2$ (XXVI). A suspension of 44 ("TriTzPyr", 1.88 g, 10.0 mmol) in MeCN (5 mL) was added to a stirred solution of [Fe(H$_2$O)$_6$][ClO$_4$]$_2$ (1.21 g, 3.33 mmol) in MeCN (5 mL). The compound 44 has the structure

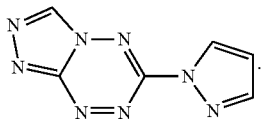

44

The solution as stirred for 15 minutes until it was a uniform blue color. Diethyl ether (10 mL) was added, and [(TriTzPyr)$_3$Fe][ClO$_4$]$_2$ (XXVI, 2.10 g, 77%) was collected as a dark blue solid via filtration. $^1$HNMR (400 mHz, d$_6$-DMSO) 6.73 (s, 1H, pyr-CH), 8.02 (s, 1H, pyr-CH), 8.92 (s, 1H, pyr-CH), 9.98 (s, 1H, triazolo-CH) δ. UV-Vis spectrum (KBr pellet) 265 (1.00), 355 (0.69), 540 (0.45), 633 (0.62), 708 (0.62) λ$_{max}$ (relative intensity). Anal. Calcd for C$_{18}$H$_{12}$Cl$_2$FeN$_{24}$O$_8$: C, 26.39%, H, 1.48%, N, 41.04%. Found: C, 26.60%, H, 1.55%, N, 41.34%.

Synthesis of [(TriTz(NO$_2$Pyr))$_3$Fe][ClO$_4$]$_2$ (XXVII). Complex XXVII can be synthesized in an analogous method by combining a suspension of 45 ("TriTz(NO$_2$Pyr)", 0.233 g, 1.00 mmol) in MeCN (2 mL) and a solution of [Fe(H$_2$O)$_6$][ClO$_4$]$_2$ (0.121 g, 0.333 mmol) in MeCN (2 mL). Compound 45 has the structure

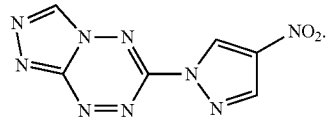

45

Diethyl ether can be added to precipitate product which can be collected via filtration.

Synthesis of [(TriTzTrz)$_3$Fe][ClO$_4$]$_2$ (XXVIII). Complex XXVIII can be synthesized in an analogous method by combining a suspension of 46 ("TriTzTrz", 0.189 g, 1.00 mmol) in MeCN (2 mL) and a solution of [Fe(H$_2$O)$_6$][ClO$_4$]$_2$ (0.121 g, 0.333 mmol) in MeCN (2 mL). Compound 46 has the structure

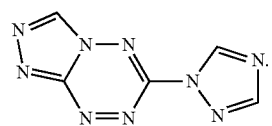

46

Diethyl ether can be added to precipitate product which can be collected via filtration.

Synthesis of [(NH$_2$TriTzDMP)$_3$Fe][ClO$_4$]$_2$ (XXIX). A solution of 47 ("NH$_2$TriTzDMP", 2.31 g, 10.0 mmol) in MeCN (5 mL) was added to a stirred solution of [Fe(H$_2$O)$_6$][ClO$_4$]$_2$ (1.21 g, 3.33 mmol) in MeCN (5 mL). The compound 47 has the structure

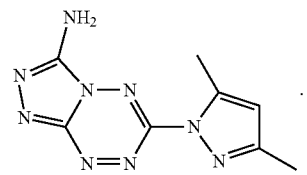

47

The solution as stirred for 15 minutes until it was a uniform blue color. Diethyl ether (10 mL) was added, and [(NH$_2$TriTzDMP)$_3$Fe][ClO$_4$]$_2$ (XXIX, 2.81 g, 89%) was collected as a dark blue solid via filtration. $^1$HNMR (400 mHz, d$_6$-DMSO) 2.10 (s, 3H, CH$_3$), 2.43 (s, 3H, CH$_3$), 6.15 (s, 1H, pyr-CH), 7.74 (s, 2H, NH$_2$) δ. UV-Vis spectrum (KBr pellet) 243 (1.00), 288 (0.98), 343 (0.64), 592 (0.44), 693 (0.53), 752 (0.55), 822 (0.56), 1010 (0.19) λ$_{max}$ (relative intensity). Anal. Calcd for C$_{24}$H$_{27}$Cl$_2$FeN$_{27}$O$_8$: C, 30.39%, H, 2.87%, N, 39.88%. Found: C, 30.35%, H, 2.92%, N, 40.19%.

Synthesis of [(NH$_2$TriTzPyr)$_3$Fe][ClO$_4$]$_2$ (XXX). A solution of 48 ("NH$_2$TriTzPyr", 2.03 g, 10.0 mmol) in MeCN (5 mL) was added to a stirred solution of [Fe(H$_2$O)$_6$][ClO$_4$]$_2$ (1.21 g, 10.0 mmol) in MeCN (5 mL). The compound 48 has the structure

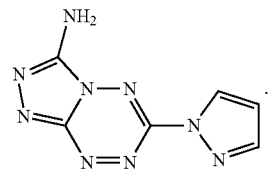

48

The solution as stirred for 15 minutes until it was a uniform blue color. Diethyl ether (10 mL) was added, and [(NH$_2$TriTzPyr)$_3$Fe][ClO$_4$]$_2$ (XXX, 2.30 g, 80%) was collected as a dark blue solid via filtration. $^1$HNMR (400 mHz, d$_6$-DMSO) 6.69 (s, 1H, pyr-CH), 7.57 (s, 2H, NH$_2$), 7.96 (s, 1H, pyr-CH), 8.79 (s, 1H, pyr-CH) δ. UV-Vis spectrum (KBr pellet) 283 (1.00), 366 (0.73), 566 (0.39), 674 (0.45), 752 (0.46), 828 (0.37), 922 (0.18) λ$_{max}$ (relative intensity). Anal. Calcd for C$_{18}$H$_{15}$Cl$_2$FeN$_{27}$O$_8$: C, 25.01%, H, 1.75%, N, 43.76%. Found: C, 25.24%, H, 1.97%, N, 43.61%.

Synthesis of [(NH$_2$TriTz(NO$_2$Pyr)$_3$Fe][ClO$_4$]$_2$ (XXXI). Complex XXXI can be synthesized in an analogous method by combining a suspension of 49 ("NH$_2$TriTz(NO$_2$Pyr)", 0.248 g, 1.00 mmol) in MeCN (2 mL) and a solution of

[Fe(H₂O)₆][ClO₄]₂ (0.121 g, 0.333 mmol) in MeCN (2 mL). Compound 49 has the structure

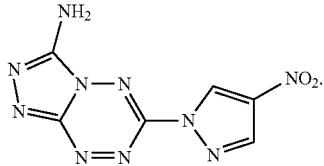

49

Diethyl ether can be added to precipitate product which can be collected via filtration.

Synthesis of [(NH₂TriTzTrz)₃Fe][ClO₄]₂ (XXXII). Complex XXXII can be synthesized in an analogous method by combining a suspension of 50 ("NH₂TriTzTrz", 0.204 g, 1.00 mmol) in MeCN (2 mL) and a solution of [Fe(H₂O)₆][ClO₄]₂ (0.121 g, 0.333 mmol) in MeCN (2 mL). Compound 50 has the structure

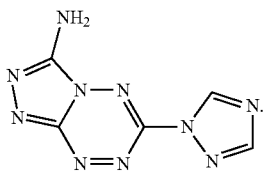

50

Diethyl ether can be added to precipitate product which can be collected via filtration.

Synthesis of [(SHTriTz(NO_Pyr))₃Fe][ClO₄]₂ (XXXIII). Complex XXXIII can be synthesized in an analogous method by combining a suspension of 51 ("SHTriTzDMP", 0.248 g, 1.00 mmol) in MeCN (2 mL) and a solution of [Fe(H₂O)₆][ClO₄]₂ (0.121 g, 0.333 mmol) in MeCN (2 mL). Compound 51 has the structure

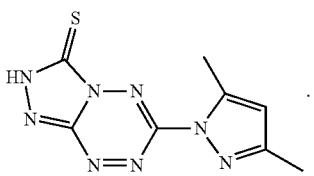

51

Diethyl ether can be added to precipitate product which can be collected via filtration.

Synthesis of [(SHTriTzTrz)₃Fe][ClO₄]₂ (XXXIV). Complex XXXIV can be synthesized in an analogous method by combining a suspension of 52 ("SHTriTzPyr", 0.20 g, 1.00 mmol) in MeCN (2 mL) and a solution of [Fe(H₂O)₆][ClO₄]₂ (0.121 g, 0.333 mmol) in MeCN (2 mL). Compound 52 has the structure

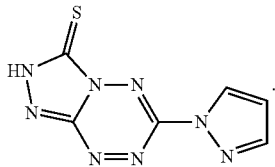

52

Diethyl ether can be added to precipitate product which can be collected via filtration.

Synthesis of [(SHTriTz(NO₂PYr))₃Fe][ClO₄]₂ (XXXV). Complex XXXV can be synthesized in an analogous method by combining a suspension of 53 ("SHTriTz(NO₂Pyr)", 0.265 g, 1.00 mmol) in MeCN (2 mL) and a solution of [Fe(H₂O)₆][ClO₄]₂ (0.121 g, 0.333 mmol) in MeCN (2 mL). Compound 53 has the structure

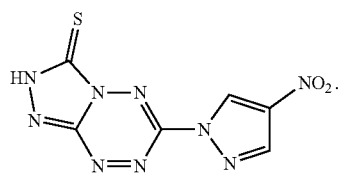

53

Diethyl ether can be added to precipitate product which can be collected via filtration.

Synthesis of [(SHTriTzTrz)₃Fe][ClO₄]₂ (XXXVI). Complex XXXVI can be synthesized in an analogous method by combining a suspension of 54 ("SHTriTzTrz", 0.221 g, 1.00 mmol) in MeCN (2 mL) and a solution of [Fe(H₂O)₆][ClO₄]₂ (0.121 g, 0.333 mmol) in MeCN (2 mL). Compound 54 has the structure

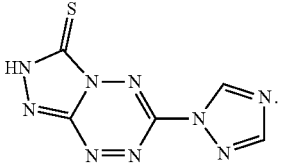

54

Diethyl ether can be added to precipitate product which can be collected via filtration.

Synthesis of [(DMPTzNH₂)₂Cu][NO₃]₂ (XXXVII). A solution of compound 23 (0.191 g, 1.00 mmol) in MeCN (5 mL) was prepared. Cu(NO₃)₂·2.5H₂O (0.116 g, 0.500 mmol) was added. The result was an orange solution, which was stirred at room temperature for 15 minutes until it was a uniform brown color. The solution was concentrated to 2 mL and diethyl ether (10 mL) was added to precipitate the product [(DMPTzNH₂)₂Cu][NO₃]₂ (XXXVII, 0.259 g, 91%) as a brown powder. Single crystals suitable for x-ray diffraction were grown from a concentrated MeCN solution at 0° C. over three days. UV-Vis spectrum (MeCN) $\lambda_{max}$ ($\epsilon_M$): 271 (47,960), 404 (6,540), 511 (2,090), 820 (br, 270) nm (L mol⁻¹ cm⁻¹). Anal. Calcd for C₁₄H₁₈CuN₁₆O₆: C, 29.51%, H, 3.18%, N, 39.32%. Found: C, 29.73%, H, 3.57%, N, 38.86.

Synthesis of [(PyrTzNH₂ 2Cu][NO₃]₂ (XXXVIII). A solution of compound 24 (0.164 g, 1.00 mmol) in MeCN (5 mL) was prepared. Cu(NO₃)₂·2.5H₂O (0.116 g, 0.500 mmol) was added. The result was an orange solution, which was stirred at room temperature for 15 minutes until it was a uniform brown color. The solution was concentrated to 2 mL and diethyl ether (10 mL) was added to precipitate the product [(PyrTzNH$_2$)$_2$Cu][NO$_3$]$_2$ (XXXVIII, 0.185 g, 72.1%) as a pale tan-green powder. Anal. Calcd for C$_{10}$H$_{10}$CuN$_{16}$O$_6$: C, 23.38%, H, 1.96%, N, 43.62%. Found: C, 23.63%, H, 1.92%, N, 43.96%.

Synthesis of [(DMPTzOH)$_2$Cu][NO$_3$]$_2$ (XXXIX). Compound XXXIX can be synthesized an analogous manner. A solution of 27 (0.192 g, 1.00 mmol) in MeCN (2 mL) can be combined with a solution of Cu(NO$_3$)$_2$.2.5H$_2$O (0.116 g, 0.500 mmol) in MeCN (2 mL). The resulting solution can be stirred for 2 hours and the product precipitated through addition of diethyl ether (20 mL).

Synthesis of [(DMPTzOH)$_2$Cu][NO$_3$]$_2$ (XL). Compound XL can be synthesized an analogous manner. A solution of 28 (0.164 g, 1.00 mmol) in MeCN (2 mL) can be combined with a solution of Cu(NO$_3$)$_2$.2.5H$_2$O (0.116 g, 0.500 mmol) in MeCN (2 mL). The resulting solution can be stirred for 2 hours and the product precipitated through addition of diethyl ether (20 mL).

Synthesis of [(DMPTzDNAZ)$_2$Cu][NO$_3$]$_2$ (XLI). A solution of compound 31 (0.321 g, 1.00 mmol) in MeCN was prepared. Cu(NO$_3$)$_2$.2.5H$_2$O (0.116 g, 0.500 mmol) was added. The resulting yellow-brown solution was stirred for 30 minutes to ensure complete reaction. Diethyl ether (20 mL) was added to precipitate the product [(DMPTzDNAZ)$_2$Cu][NO$_3$]$_2$ (XLI, 0.367 g, 81%). Crystals suitable for single crystal X-ray diffraction were grown by the slow diffusion of diethyl ether into a concentrated MeCN solution of XLI at 0° C. UV-Vis spectrum (MeCN) $\lambda_{max}$ ($\varepsilon_M$): 275 (49,280), 394 (6,060), 519 (2,100), 810 (br, 250) nm (L mol$^{-1}$ cm$^{-1}$).

Synthesis of [(PyrTzDNAZ)$_2$Cu][NO$_3$]$_2$ (XLII). A solution of compound 32 (0.293 g, 1.00 mmol) in MeCN was prepared. Cu(NO$_3$)$_2$.2.5H$_2$O (0.116 g, 0.500 mmol) was added. The resulting yellow-brown solution was stirred for 30 minutes to ensure complete reaction. Diethyl ether (20 mL) was added to precipitate the product [(PyrTzDNAZ)$_2$Cu][NO$_3$]$_2$ (XLII, 0.279 g, 72%). Anal. Calcd for C$_{16}$H$_{14}$CuN$_{20}$O$_{14}$: C, 24.83%, H, 1.82%, N, 36.20%. Found: C, 24.86%, H, 2.09%, N, 35.95.

Synthesis of [(DMPTzPETriN)$_2$Cu][NO$_3$]$_2$ (XLIII). Compound XLIII can be synthesized an analogous manner. A solution of 35 (0.445 g, 1.00 mmol) in MeCN (2 mL) can be combined with a solution of Cu(NO$_3$)$_2$.2.5H$_2$O (0.116 g, 0.500 mmol) in MeCN (2 mL). The resulting solution can be stirred for 2 hours and the product precipitated through addition of diethyl ether (20 mL).

Synthesis of [(DMPTzPETriN)$_2$Cu][NO$_3$]$_2$ (XLIV). Compound XLIV can be synthesized an analogous manner. A solution of 36 (0.417 g, 1.00 mmol) in MeCN (2 mL) can be combined with a solution of Cu(NO$_3$)$_2$.2.5H$_2$O (0.116 g, 0.500 mmol) in MeCN (2 mL). The resulting solution can be stirred for 2 hours and the product precipitated through addition of diethyl ether (20 mL).

Synthesis of [(DMPTzTrisN)$_2$Cu][NO$_3$]$_2$ (XLV). Compound XLV can be synthesized an analogous manner. A solution of 39 (0.445 g, 1.00 mmol) in MeCN (2 mL) can be combined with a solution of Cu(NO$_3$)$_2$.2.5H$_2$O (0.116 g, 0.500 mmol) in MeCN (2 mL). The resulting solution can be stirred for 2 hours and the product precipitated through addition of diethyl ether (20 mL).

Synthesis of [(DMPTzTrisN)$_2$Cu][NO$_3$]$_2$ (XLVI). Compound XLVI can be synthesized an analogous manner. A solution of 40 (0.417 g, 1.00 mmol) in MeCN (2 mL) can be combined with a solution of Cu(NO$_3$)$_2$.2.5H$_2$O (0.116 g, 0.500 mmol) in MeCN (2 mL). The resulting solution can be stirred for 2 hours and the product precipitated through addition of diethyl ether (20 mL).

Synthesis of [(DMPTzNH$_2$)Cu(NO$_3$)$_2$]$_2$ (XLVII). To a solution of 23 (1.92 g, 10.0 mmol) in MeCN (10 mL) was added Cu(NO$_3$)$_2$.2.5H$_2$O (2.32 g, 10.0 mmol). The solution was stirred for 3 hours at 40° C. until a pale green powder precipitated from solution. The powder was collected by filtration and identified as [(DMPTzNH$_2$)Cu(NO$_3$)$_2$]$_2$ (XLVII, 2.91 g, 77%). Anal. Calcd for C$_{14}$H$_{18}$Cu$_2$N$_{18}$O$_{12}$: C, 22.20%, H, 2.40%, N, 33.29%. Found: C, 21.91%, H, 2.46%, N, 33.13.

Synthesis of [(DMPTzOH)Cu(NO$_3$)$_2$]$_2$ (XLVIII). Complex XLVIII can be synthesized in an analogous manner. A solution of 27 (0.192 g, 1.00 mmol) in MeCN (5 mL) can be added to a solution of Cu(NO$_3$)$_2$.2.5H$_2$O (0.232 g, 1.00 mmol) in MeCN (5 mL). The resulting solution can be stirred for 3 hours at 40° C. until product precipitates.

Synthesis of [(DMPTzDNAZ)Cu(NO$_3$)$_2$]$_2$ (XLIX). To a solution of 31 (1.60 g, 5.0 mmol) in MeCN (10 mL) was added Cu(NO$_3$)$_2$.2.5H$_2$O (1.16 g, 5.0 mmol). The solution was stirred for 3 hours at 40° C. until a tan powder precipitated from solution. The powder was collected by filtration and identified as [(DMPTzDNAZ)Cu(NO$_3$)$_2$]$_2$ (XLIX, 1.83 g, 77%). Anal. Calcd for C$_{20}$H$_{22}$Cu$_2$N$_{22}$O$_{20}$: C, 23.61%, H, 2.18%, N, 30.29%. Found: C, 23.91%, H, 2.09%, N, 30.38.

Synthesis of [(DMPTzPETriN)Cu(NO$_3$)$_2$]$_2$ (L). Complex L can be synthesized in an analogous manner. A solution of 35 (0.445 g, 1.00 mmol) in MeCN (5 mL) can be added to a solution of Cu(NO$_3$)$_2$.2.5H$_2$O (0.232 g, 1.00 mmol) in MeCN (5 mL). The resulting solution can be stirred for 3 hours at 40° C. until product precipitates.

Synthesis of [(DMPTzTrisN)Cu(NO$_3$)$_2$]$_2$ (LI). Complex LI can be synthesized in an analogous manner. A solution of 39 (0.430 g, 1.00 mmol) in MeCN (5 mL) can be added to a solution of Cu(NO$_3$)$_2$.2.5H$_2$O (0.232 g, 1.00 mmol) in MeCN (5 mL). The resulting solution can be stirred for 3 hours at 40° C. until product precipitates.

Synthesis of [(DMPTzNH$_2$)$_2$Cu][PF$_6$] (LII). A solution of compound 23 (0.191 g, 1.00 mmol) in MeCN (5 mL) was prepared. [Cu(MeCN)$_4$][PF$_6$] (0.186 g, 0.500 mmol) was added. The resulting orange solution was stirred at room temperature for 15 minutes until it was a uniform purple color. The solution was concentrated to 2 mL and diethyl ether (10 mL) was added to precipitate the product [(DMPTzNH$_2$)$_2$Cu][NO$_3$]$_2$ (LII, 0.259 g, 91%) as a brown powder. Single crystals suitable for X-ray diffraction were grown from a concentrated MeCN solution at 0° C. over three days. $^1$HNMR (400 MHz, d$_6$-acetone) δ 6.86 (s, 2H, NH$_2$), 6.45 (s, 2H, Pyr-H), 2.71 (s, 3H, CH$_3$), 2.33 (s, 3H, CH$_3$). UV-Vis spectrum (MeCN) $\lambda_{max}$ ($\varepsilon_M$): 273 (47,450), 401 (6,510), 509 (3,000) nm (L mol$^{-1}$ cm$^{-1}$). Anal. Calcd for C$_{14}$H$_{18}$CuF$_6$N$_{14}$P: C, 28.08%, H, 3.03%, N, 32.74%. Found: C, 27.76%, H, 3.34%, N, 32.95%.

Synthesis of [(DMPTzDNAZ)$_2$Cu][PF$_6$] (LIII). A solution of compound 31 (0.321 g, 1.00 mmol) in MeCN (5 mL) was prepared. [Cu(MeCN)$_4$][PF$_6$] (0.186 g, 0.500 mmol) was added. The resulting brown solution was stirred for 30 minutes. Diethyl ether (20 mL) was added to precipitate the product [(DMPTzDNAZ)$_2$Cu][PF$_6$] (LIII, 0.318 g, 88%) as a brown powder. Crystals suitable for single crystal X-ray diffraction were grown by cooling a concentrated MeCN solution at 0° C. for 3 days. $^1$HNMR (400 MHz, d$_6$-acetone) δ 6.42 (s, 1H, Pyr-H), 5.37 (s, 4H, CH$_2$), 2.79 (s, 3H, CH$_3$), 2.41 (s, 3H, CH$_3$). UV-Vis spectrum (MeCN) $\lambda_{max}$ ($\varepsilon_M$): 270 (48,810), 397 (5,720), 520 (2,550) nm (L mol$^{-1}$ cm$^{-1}$).

Synthesis of [(DMPTzNH$_2$)$_2$Co(H$_2$O)(NO$_3$)][NO$_3$] (LIX). A solution of compound 23 (0.191 g, 1.00 mmol) in MeCN (5 mL) was prepared. Co(NO$_3$)$_2$.6H$_2$O (0.145 g, 0.500 mmol) was added. The resulting orange solution was stirred at room temperature for 15 minutes until it was a uniform dark brown color. The solution was concentrated to 2 mL and diethyl ether (10 mL) was added to precipitate the product [(DMPTzNH$_2$)$_2$Co(H$_2$O)(NO$_3$)][NO$_3$] (LIX, 0.257 g, 83%) as a brown powder. Single crystals suitable for X-ray diffraction were grown from a concentrated MeCN solution at 0° C. over three days. UV-Vis spectrum (MeCN) $\lambda_{max}$ ($\varepsilon_M$): 267 (48,770), 395 (5,130), 507 (2,280) nm (L mol$^{-1}$ cm$^{-1}$). Elemental analysis calculated for C$_{14}$H$_{20}$CoN$_{16}$O$_7$: C, 28.83%, H, 3.46%, N, 38.42%. Found: C, 28.63%, H, 3.58%, N, 38.09%.

Synthesis of [(DMPTzDNAZ)$_2$Co(H$_2$O)$_2$][NO$_3$]$_2$ (LX). A solution of compound 31 (0.321 g, 1.00 mmol) in THF (5 mL) was prepared. Co(NO$_3$)$_2$.6H$_2$O (0.145 g, 0.500 mmol) was added. The resulting orange-brown solution was stirred for an additional 30 minutes to ensure complete reaction. Hexane (10 mL) was added to precipitate the product [(DMPTzDNAZ)$_2$Co(H$_2$O)$_2$][NO$_3$]$_2$ (LX, 0.327 g, 77%) as a brown powder. Single crystals suitable for X-ray diffraction were grown by the slow diffusion of hexane into a concentrated THF solution at 0° C. UV-Vis spectrum (MeCN) $\lambda_{max}$ ($\varepsilon_M$): 272 (47,340), 402 (5,010), 509 (2,550) nm (L mol$^{-1}$ cm$^{-1}$). Elemental analysis calculated for C$_{20}$H$_{26}$CoN$_{20}$O$_{16}$: C, 27.88%, H, 3.04%, N, 32.52%. Found: C, 28.13%, H, 2.86%, N, 32.24%.

Synthesis of [(DMPTzNH$_2$)$_3$Ni][NO$_3$]$_2$ (LXI). A solution of compound 23 (0.191 g, 1.00 mmol) in MeCN (5 mL) was prepared. Ni(NO$_3$)$_2$.6H$_2$O (0.097 g, 0.333 mmol) was added. The initially orange solution was stirred at room temperature for 15 minutes until it turned a uniform yellow-brown color. The solution was concentrated to 2 mL and diethyl ether (10 mL) was added to precipitate the product [(DMPTzNH$_2$)$_3$Ni][NO$_3$]$_2$ LXI (0.199 g, 79%) as a yellow powder. Single crystals suitable for X-ray diffraction were grown from a concentrated MeCN solution at 0° C. over three days. UV-Vis spectrum (MeCN) $\lambda_{max}$($\varepsilon_M$): 268 (78,780), 428 (10,560), 510 (3,690), 660 (90) nm (L mol$^{-1}$ cm$^{-1}$). Elemental analysis calculated for C$_{21}$H$_{27}$N$_{23}$NiO$_6$: C, 33.36%, H, 3.60%, N, 42.59%. Found: C, 33.38%, H, 3.86%, N, 42.26%.

Synthesis of [(DMPTzDNAZ)$_2$Ni(H$_2$O)$_2$][NO$_3$]$_2$ (LXII). A solution of compound 31 (0.321 g, 1.00 mmol) in THF (5 mL) was prepared. Ni(NO$_3$)$_2$.6H$_2$O (0.097 g, 0.333 mmol) was added. The resulting yellow solution was stirred for 30 minutes to ensure complete reaction. Hexane (10 mL) was added to precipitate the product [(DMPTzDNAZ)$_2$Ni(H$_2$O)$_2$][NO$_3$]$_2$ (LXI, 0.310 g, 72%) as a yellow brown powder. Single crystals suitable for X-ray diffraction were grown by cooling a concentrated THF solution at 0° C. over 1 week. UV-Vis spectrum (MeCN) $\lambda_{max}$ ($\varepsilon_M$): 278 (47,960), 409 (5,220), 499 (3,740), 670 (85), 775 (65) nm (L mol$^{-1}$ cm$^{-1}$). Elemental analysis calculated for C$_{22}$H$_{30}$N$_{20}$NiO$_{16.5}$ (compound analyzed as 0.5 THF adduct): C, 29.45%, H, 3.37%, N, 31.22%. Found: C, 29.53%, H, 3.01%, N, 31.42%.

Complexes of 3-amino-6-(3,5-dimethylpyrazole)tetrazine) (23, "NH$_2$TzDMP") and 3-(3,3'-dinitroazetidine),6-(3,5-dimethylpyrazole) tetrazine) (24, "DNAZTzDMP") with first row transition metal centers were synthesized. Reactions of Fe$^{II}$(H$_2$O)$_6$(BF$_4$)$_2$ and Fe(NO$_3$)$_3$ 9H$_2$O with 23 and 8 led to complexes of the form [(RTzDMP)$_3$Fe]X$_2$ (X=BF$_4$, R=NH$_2$, DNAZ; X=NO$_3$, R=NH$_2$, DNAZ). Their UV-vis spectra included intense MLCT bands. Ligands 23 and 8 react with Cu$^{II}$(NO$_3$)$_2$.5/2H$_2$O to form [(RTzDMP)$_2$Cu(NO$_3$)][NO$_3$] (R=NH$_2$, DNAZ). Ligands 23 and 8 also react with Cu$^{I}$(CH$_3$CN)$_4$(PF$_6$) to form [(RTzDMP)$_2$Cu][PF$_6$] (R=NH$_2$, DNAZ). Ligands 23 and 24 react with Co(NO$_3$)$_2$.6H$_2$O and Ni(NO$_3$)$_2$.6H$_2$O to form [(NH$_2$TzDMP)$_2$Co(H$_2$O)(NO$_3$)][NO$_3$], [(DNAZTzDMP)$_2$Co(H$_2$O)$_2$][NO$_3$]$_2$, [(NH$_2$TzDMP)$_3$Ni][NO$_3$]$_2$, and [(DNAZTzDMP)$_2$Ni(H$_2$O)$_2$][NO$_3$]$_2$. Thus, a variety of coordination compounds that contain complexes of pyrazole tetrazine ligands with late first row transition metal centers were prepared. At least some of these complexes are photoactive or believed to be photoactive.

Other Embodiment Photoactive Compounds.

Another embodiment is a composition of the formula

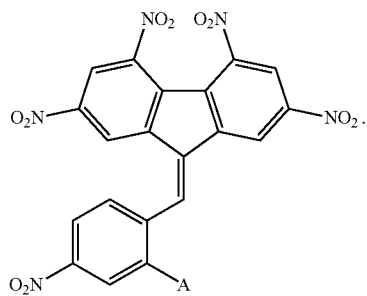

In an embodiment, A is hydrogen. In another embodiment, A is NO$_2$. The compounds can be synthesized by condensing 4-nitro-benzaldehyde or 2,4-dinitro-benzaldehyde with 2,4,5,7-tetranitrofluorene at elevated temperatures in appropriate solvents.

Another embodiment is a composition of the formula

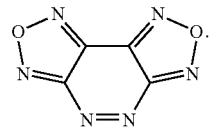

Another embodiment is a composition of the formula

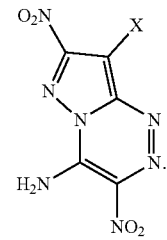

Another embodiment is a composition of the formula

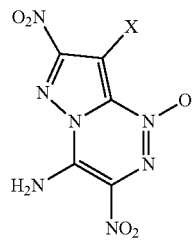

wherein X is H or NO$_2$.

Embodiment photoactive explosives are potentially insensitive to conventional stimuli (e.g. spark, impact, friction) and initiate from a UV laser or VIS laser source (and a near-IR laser for suitable photoactive coordination compounds that are suitable because they absorb the laser light from a suitable near-IR laser) that promptly produces photochemical reactions that lead to direct optical initiation of the material. These materials may provide an enhanced safety envelope for use because they can also be tailored to react with only specific laser wavelengths and pulse durations that act as a key for safe use.

Initiation of embodiment photoactive materials using lasers. The photoactive explosives may be initiated through a range of laser wavelengths and pulse durations. Pulsed lasers in the range from 5 fs to 100 ns could be used for applications with critical timing. Lasers ranging from 100 ns to continuous wave (CW) duration could be used to initiate the explosives for applications where timing is less important. Similarly, high intensities ($10^6$ to $10^{14}$ W/cm$^2$) are required for timing critical applications to ensure rapid (<100 ns) initiation, while low intensity (<$10^6$ W/cm$^2$) irradiation can lead to thermal ignition.

Suitable lasers for initiation of materials with absorbance in the near infrared region include Nd:YAG with a wavelength of 1064 nm and pulse durations from ps to CW; Nd:YVO$_4$ with a wavelength of 1064 nm and pulse durations from ns to CW; Ti:sapphire with wavelengths ranging from 650 nm to 1100 nm and pulse durations from fs to CW; diode lasers—such as GaAlAs with a wavelength of 808 nm or 785 nm and a pulse duration of CW; fiber lasers—such as ytterbium with wavelengths from 1030 nm to 1100 nm, Erbium with a wavelength of 1550 nm and pulse durations from fs to CW.

Suitable lasers for initiation of materials with absorbance in the visible region include frequency doubled Nd:YAG and Nd:YVO$_4$ with a wavelength of 532 nm and pulse durations of ns to CW; Frequency doubled Ti:sapphire with wavelengths of 350 nm to 450 nm and pulse durations of fs to CW; Frequency doubled fiber lasers; Diode lasers—such as InGaN with a wavelength of 405 nm and a pulse duration of CW.

Suitable lasers for initiation of materials with absorbance in the ultra-violet region include frequency tripled Nd:YAG and Nd:YVO$_4$ with wavelengths of 355 nm and pulse durations of ps to CW; frequency tripled Ti:sapphire with a wavelength of 266 nm with pulse durations of fs to CW; frequency quadrupled Nd:YAG with a wavelength of 266 nm and a pulse duration of ps to CW; excimer lasers (ArF wavelength of 193 nm, KrF 248 wavelength of nm, XeCl wavelength of 308 nm, XeF 351 wavelength of nm) and a pulse duration of 10-100 ns.

Embodiment energetic materials were prepared. They may absorb photons from a laser source to produce photochemical reactions in the material that lead to explosive initiation and detonation. At least some of the embodiment materials are believed to be less sensitive and safer to handle than conventional energetic materials. They may also be more reliable than known materials, utilize lower laser fluences to take advantage of more compact and portable turnkey systems, and can be tailored to initiate through a non-linear optical response mechanism that adds an additional safety feature to prevent accidental or illicit detonation.

Although the embodiments have been described with reference to specific details, it is not intended that such details should be regarded as limitations except as and to the extent that they are included in the accompanying claims.

What is claimed is:

1. A compound of the formula

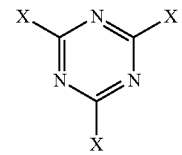

wherein X is selected from —OCH(ONO$_2$)$_2$ or

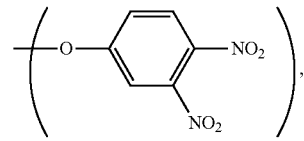

or of the formula

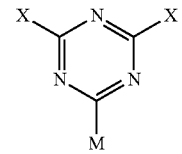

wherein X is selected from —OCH$_2$C(CH$_2$ONO$_2$)$_3$, —OCH$_2$C((F)(NO$_2$)$_2$), —OCH(ONO$_2$)$_2$,

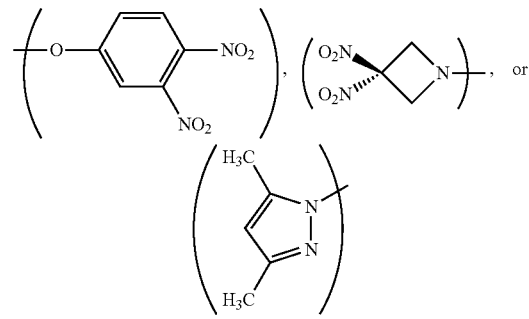

and wherein M is

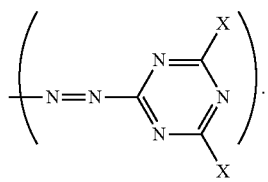

2. A coordination compound comprising:
a cationic complex comprising a transition metal center and one or more ligands coordinated to the transition metal center, wherein the one or more ligands comprise a 1,2,4,5-tetrazine ring and one or more explosive pendant groups covalently bonded to the 1,2,4,5-tetrazine ring or a 1,3,5-triazine ring and one or more explosive pendant groups covalently bonded to the 1,3,5-triazine ring;
and
a counterion,
wherein the one or more ligands have the formula:

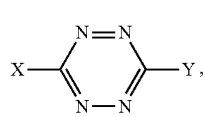

wherein X is selected from

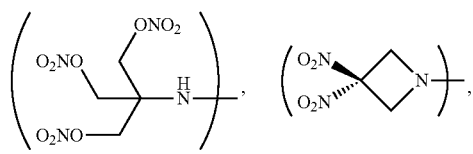

OCH$_2$C(CH$_2$ONO$_2$)$_3$, OH, or NH$_2$; and
wherein Y is selected from

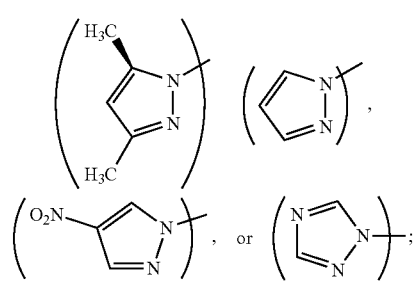

or have the formula:

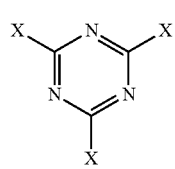

wherein X is selected from —OCH$_2$C(CH$_2$ONO$_2$)$_3$, —OCH$_2$C((F)(NO$_2$)$_2$), —OCH(ONO$_2$)$_2$,

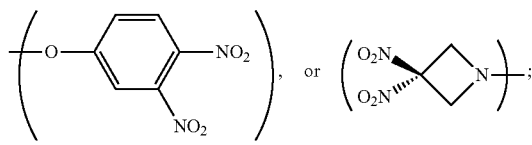

or have the formula:

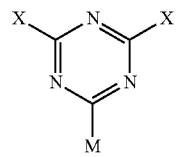

wherein X is selected from —OCH$_2$C(CH$_2$ONO$_2$)$_3$, —OCH$_2$C((F)(NO$_2$)$_2$), —OCH(ONO$_2$)$_2$,

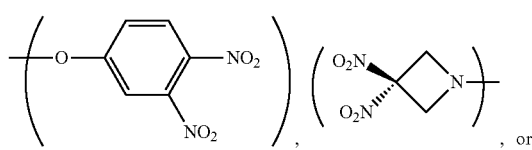

and
wherein M is

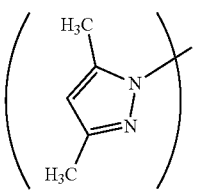

3. The coordination compound of claim 2, wherein the transition metal center comprises Fe, Cu, Ni, or Co.

4. The coordination compound of claim 2,
wherein the transition metal is Fe,
wherein the cationic complex comprises the formula Fe(II)(L)$_3^{2+}$, wherein L is a ligand selected from

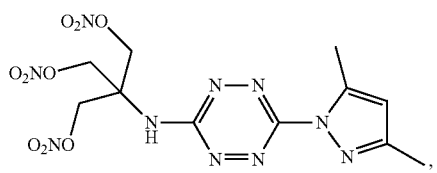

-continued

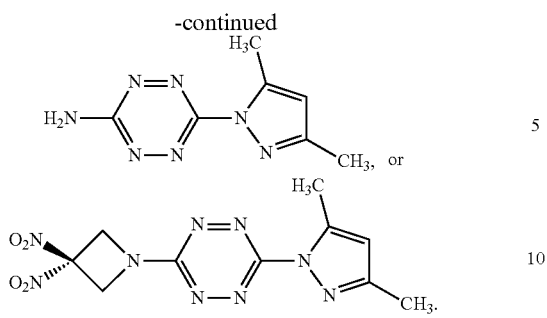

5. The coordination compound of claim 2,
wherein the transition metal is selected from Cu, Co, and Ni,
wherein the transition metal is bonded to two ligands each of which ligands has the formula

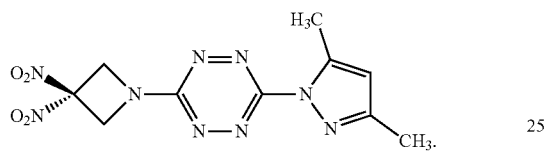

6. The coordination compound of claim 2, wherein the counterion is selected from tetrafluoroborate ($BF_4^{-1}$), nitrate ($NO_3^{-1}$), perchlorate ($ClO_4^{-1}$), sulfate ($SO_4^{-2}$), phosphate ($PO_4^{3-}$), and carbonate ($CO_3^{2-}$).

* * * * *